US010745664B2

(12) United States Patent
Bopardikar et al.

(10) Patent No.: US 10,745,664 B2
(45) Date of Patent: Aug. 18, 2020

(54) METHOD OF PROGENITOR CELL ISOLATION FROM DIFFERENT ORGANS BY NATURAL DESTRUCTION OF EXTRACELLULAR MATRIX

(71) Applicant: Reelabs Private Limited, a Company Incorporated Under Provisions of The Companies Act 1956, Mumbai (IN)

(72) Inventors: Abhijit Bopardikar, Mumbai (IN); Rohit Kulkarni, Mumbai (IN); Sunil Pophale, Mumbai (IN); Andrii Kukharchuk, Mumbai (IN); Oleksandr Kukharchuk, Mumbai (IN); Padma Priya Anand Baskaran, Mumbai (IN)

(73) Assignee: Reelabs Private Limited, a Company Incorporated Under Provisions of The Companies Act 1956, Mumbai (IN)

( * ) Notice: Subject to any disclaimer, the term of this patent is extended or adjusted under 35 U.S.C. 154(b) by 204 days.

(21) Appl. No.: 15/338,229

(22) Filed: Oct. 28, 2016

(65) Prior Publication Data
US 2018/0119093 A1    May 3, 2018

(51) Int. Cl.
| A01N 63/00 | (2020.01) |
| A61K 48/00 | (2006.01) |
| C12N 5/073 | (2010.01) |
| A01N 1/02 | (2006.01) |

(52) U.S. Cl.
CPC ......... *C12N 5/0605* (2013.01); *A01N 1/0221* (2013.01); *A01N 1/0284* (2013.01); *C12N 2500/84* (2013.01); *C12N 2509/00* (2013.01); *C12N 2533/90* (2013.01)

(58) Field of Classification Search
CPC .................................................. C12N 5/0605
See application file for complete search history.

(56) References Cited

U.S. PATENT DOCUMENTS

| 2005/0048046 A1* | 3/2005 | Kiss .......................... A61K 8/66 424/94.6 |
| 2006/0182724 A1 | 8/2006 | Riordan |
| 2010/0144027 A1 | 6/2010 | Lee et al. |

FOREIGN PATENT DOCUMENTS

| CN | 102146359 A | 8/2011 |
| WO | PCTIB2016001631 | 10/2016 |

OTHER PUBLICATIONS

Ministry of Health and Family Welfare, "The Medical Termination of Pregnancy Rules, 2003", New Delhi, Jun. 13, 2003, pp. 18-26.*
Moser et al., "Protection of the Transplant Kidney from Preservation Injury by Inhibition of Matrix Metalloproteinases", PLoS One, Jun. 21, 2016, 11(6), pp. 1-20.*
Gridelli et al., "Efficient Human Fetal Liver Cell Isolation Protocol Based on Vascular Perfusion for Liver Cell-Based Therapy and Case Report on Cell Transplantation", Liver Transplantation, 2012, vol. 18, pp. 226-237.*
Mongarden et al., "Pharmacological optimization of tissue perfusion", British Journal of Anaesthesia, 2009, 103(1), pp. 82-88.*
Srikanth et al., "Fetal cardiac mesenchymal stem cells express embryonal markers and exhibit differentiation into cells of all three germ layers", World Journal of Stem Cells, 2013, 5(1), pp. 26-33.*
Nair et al., "Final Report on the Safety Assessment of Human Placental Protein, Hydrolyzed Human Placental Protein, Human Placental Enzymes, Human Placental Lipids, Human Umbilical Extract, Placental Protein, Hydrolyzed Placental Protein, Placental Enzymes, Placental Lipids, and Umbilical Extract". International.*
Shin et al., "Culture and in vitro hepatogenic differentiation of placenta-derived stem cells, using placental extract as an alternative to serum", Cell Proliferation, 2010, vol. 43, pp. 435-444. (Year: 2010).*
Potdar, P., et al., "Development and Molecular Characterization of Human Placental Mesenchymal Stem Cells from Human Aborted Fetal Tissue as a Model to Study Mechanism of Spontaneous Abortion," Advances in Stem Cells, vol. 2014, 2014, pp. 1-17.
Sharma, K. et al., "Immunoglobulin isotype isolated from human placental extract does not interfere in complement-mediated bacterial opsonization within the wound milieu," FEBS Open Bio 5, 2015, pp. 369-377.

* cited by examiner

*Primary Examiner* — Valarie E Bertoglio
(74) *Attorney, Agent, or Firm* — Rahman LLC

(57) ABSTRACT

The present invention is directed to novel methods comprising the isolation of viable fetal progenitor cells from organs of aborted fetus. The invention comprises the use of natural proteolytic, collagenolytic and fibrinolytic activity of autologous abortive placenta tissue extract.

8 Claims, 30 Drawing Sheets

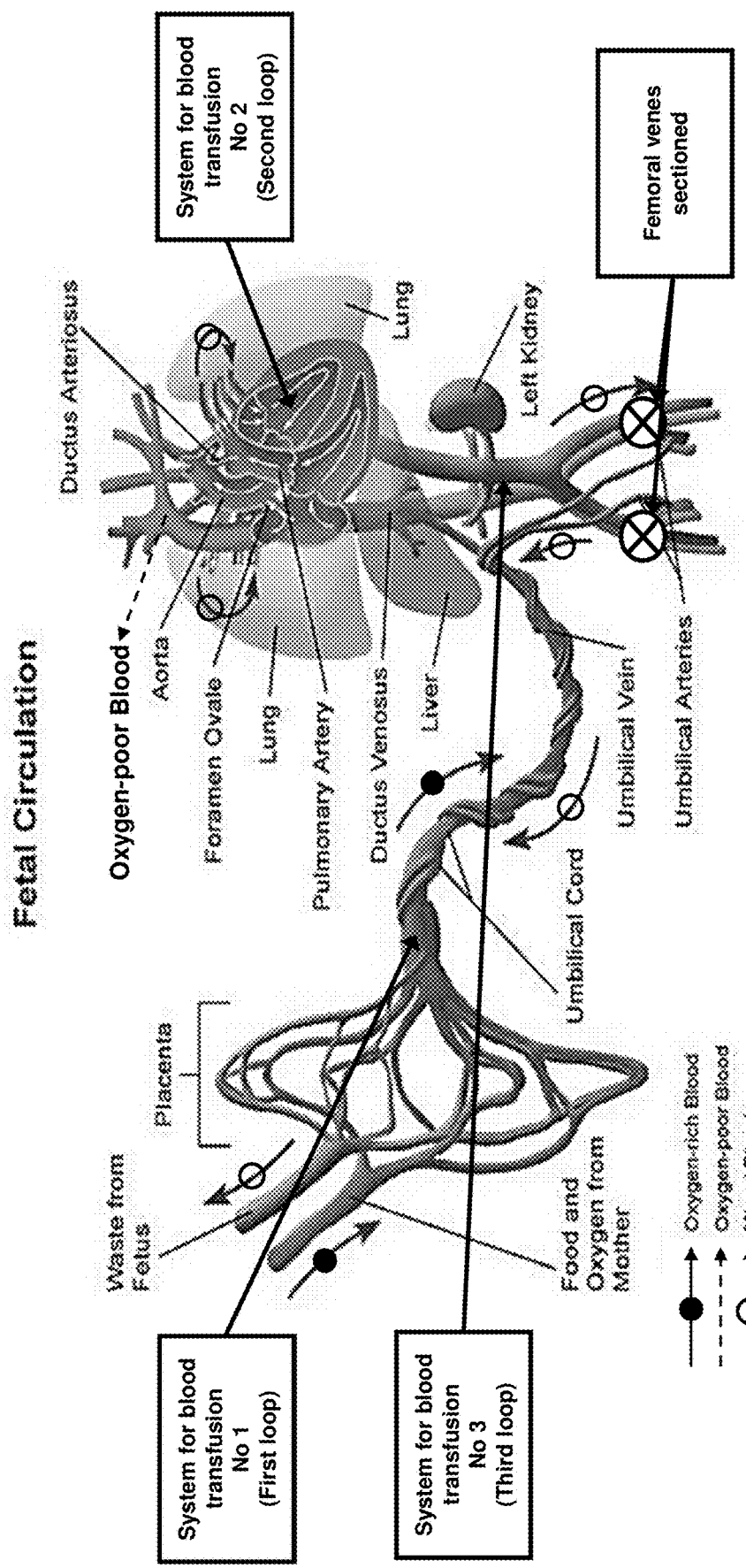
FIG. 1 Three open-loops blood supply system of fetus organs perfusion *in situ*

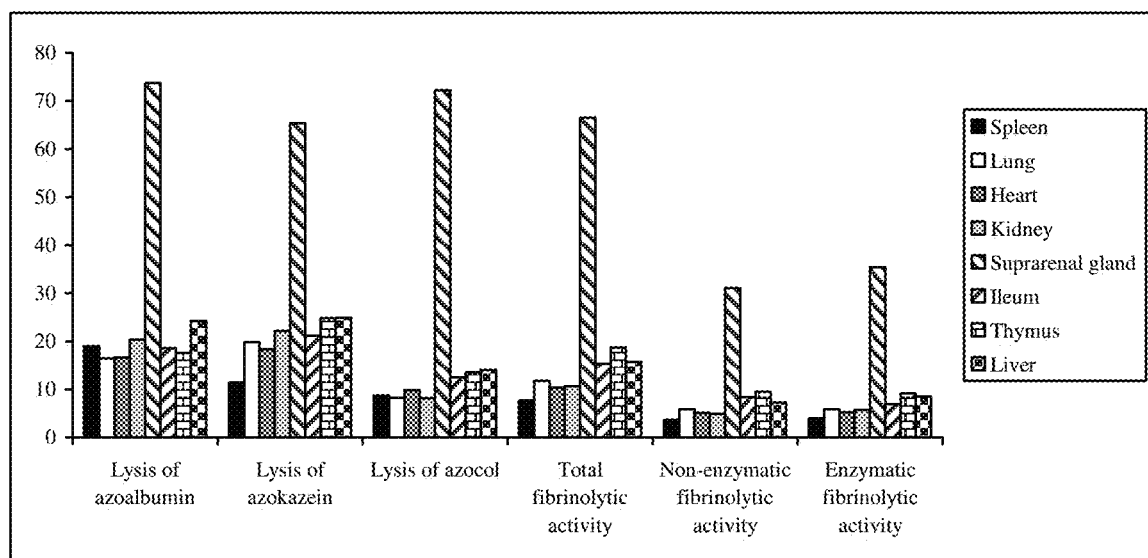
FIG. 2 Proteolytic and fibrinolitic activity in tissues of fetal intact organs
(µg/1 g tissue per 1 h)

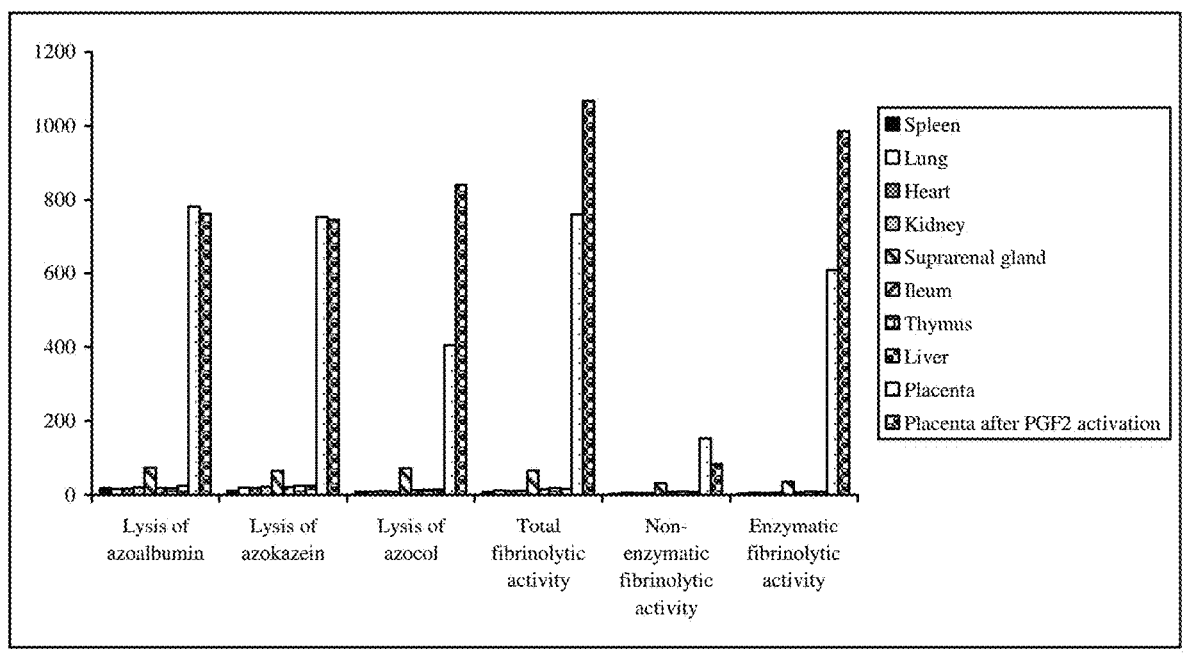
FIG. 3 Comparison the proteolytic and fibrinolitic activity in tissues of fetal intact organs and abortive placenta of the same foetuses (µg/1 g tissue per 1 h)

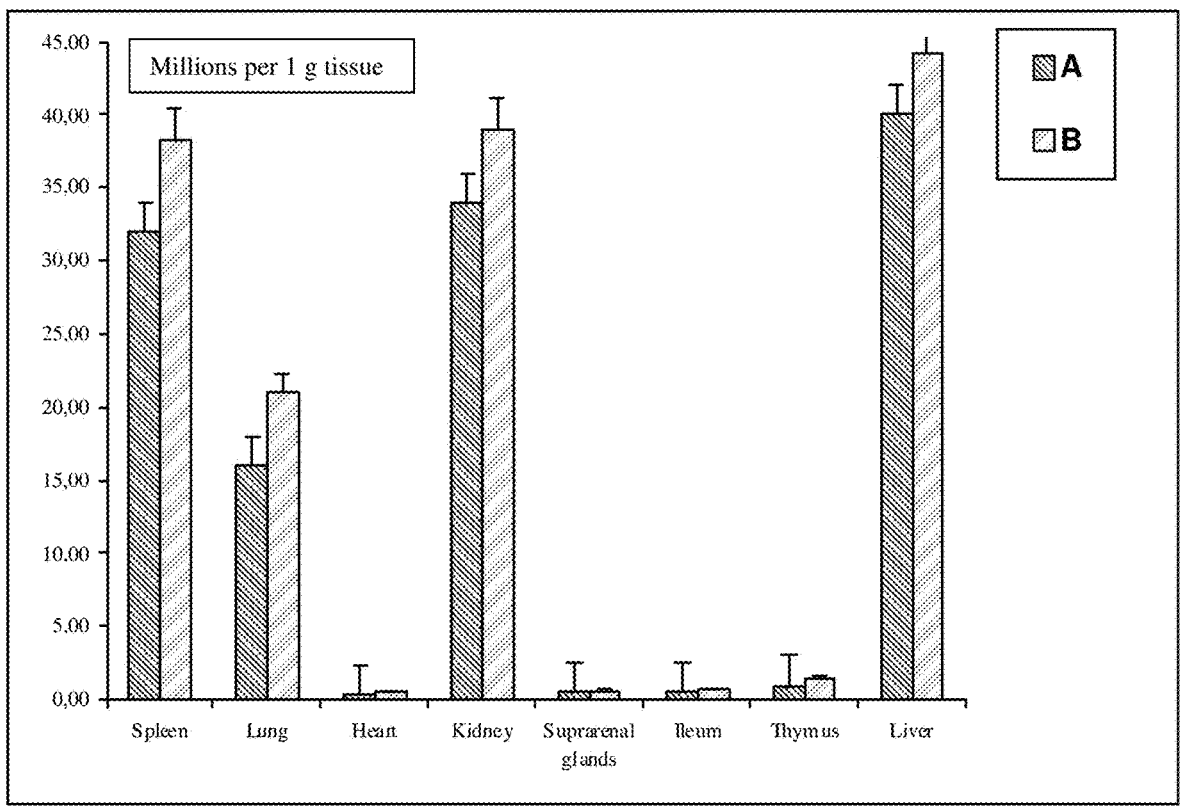
Remarks: A – native placenta extract; B – PGF2α-treated placenta extract
FIG. 4 Total amount of progenitor cells, isolated from organs of the aborted fetuses

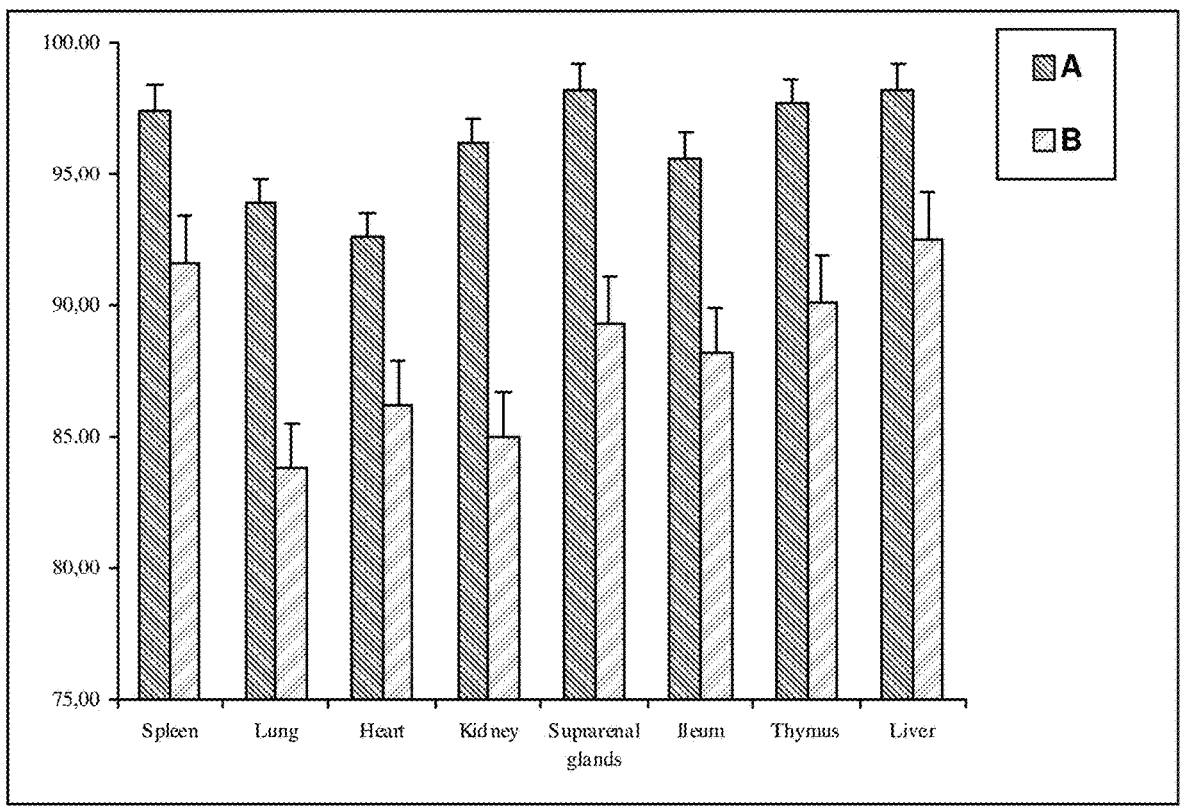
FIG. 5 Percent of viable progenitor cells, isolated from organs of the aborted fetus

| Group | TCA $\times 10^6$ | Spl $\times 10^6$ | Lg $\times 10^6$ | Cor $\times 10^5$ | Ren $\times 10^6$ | Sr $\times 10^5$ | Il $\times 10^5$ | Th $\times 10^5$ | Hp $\times 10^6$ | Number of rats in group | | Route of administration | Study duration days |
|---|---|---|---|---|---|---|---|---|---|---|---|---|---|
| | | | | | | | | | | male | female | | |
| Control group | PBS | - | - | - | - | | - | - | - | 10 | 10 | IV | 14 |
| Dose 1 | 7.77 | 2.0 | 1.0 | 0.625 | 2.0 | 0.625 | 0.75 | 0.625 | 2.5 | 11 | 12 | IV | 14 |
| Dose 2 | 15.53 | 4.0 | 2.0 | 1.25 | 4.0 | 1.25 | 1.5 | 1.25 | 5.0 | 12 | 11 | IV | 14 |
| Dose 3 | 31.05 | 8.0 | 4.0 | 2.5 | 8.0 | 2.5 | 3.0 | 2.5 | 10.0 | 15 | 15 | IV | 14 |

*Remarks:* TCA – total cells amount, Spl – spleen progenitor cells, Lg – lung progenitor cells, Cor – heart progenitor cells, Ren – kidney progenitor cells, Sr – suprarenal glands progenitor cells, Il – ileum progenitor cells, Th – thymus progenitor cells, Hp – liver progenitor cells.

FIG. 6 Design of Single-dose Toxicity studies in rats after intravenous fetal progenitor cells injections

| Group | Signs of intoxication | Body weight (+) or (−) gm comparison to study begining | Pathological changes of organs |
|---|---|---|---|
| *Control group* n=20 | No | +15.3±4.4 | No |
| *Dose 1* n=23 | No | +14.2±3.9 $p>0.05$ | No |
| *Dose 2* n=23 | No | +16.1±2.6 $p>0.05$ | No |
| *Dose 3* n=30 | No | +18.7±3.0 $p>0.05$ | No |

*Remarks:* p -- Level of reliability of various parameters corresponding to control group. n -- Number of rats in the groups.

FIG. 7 Results of Single-dose Toxicity studies in rats after intravenous fetal progenitor cells injections

| No | Organs | Control Group n=20 | Dose 1 n=23 | Dose 2 n=23 | Dose 3 n=30 |
|---|---|---|---|---|---|
| 1 | Brain* g/100 g b. wt. | 1.66±0.07 | 1.59±0.07 p>0.05 | 1.70±0.10 p>0.05 | 1.68±0.11 p>0.05 |
| 2 | (Spinal Cord) | normal | no changes | no changes | no changes |
| 3 | Eye | normal | no changes | no changes | no changes |
| 4 | (Middle Ear) | normal | no changes | no changes | no changes |
| 5 | Thyroid | normal | no changes | no changes | no changes |
| 6 | (Parathyroid) | normal | no changes | no changes | no changes |
| 7 | Spleen* g/100 g b. wt. | 0.70±0.08 | 0.65±0.07 p>0.05 | 0.75±0.09 p>0.05 | 0.78±0.05 p>0.05 |
| 8 | Thymus* g/100 g b. wt. | 0.021±0.004 | 0.023±0.006 p>0.05 | 0.019±0.005 p>0.05 | 0.020±0.004 p>0.05 |
| 9 | Adrenal* g/100 g b. wt. | 0.028±0.003 | 0.031±0.003 p>0.05 | 0.029±0.004 p>0.05 | 0.034±0.005 p>0.05 |
| 10 | (Pancreas) | normal | no changes | no changes | no changes |
| 11 | (Trachea) | normal | no changes | no changes | no changes |
| 12 | Lung* g/100 g b. wt. | 2.88±0.07 | 2.75±0.10 p>0.05 | 2.79±0.07 p>0.05 | 2.97±0.06 p>0.05 |
| 13 | Heart* g/100 g b.w. | 0.93±0.06 | 0.90±0.04 p>0.05 | 0.95±0.07 p>0.05 | 0.99±0.08 p>0.05 |
| 14 | Aorta | normal | no changes | no changes | no changes |
| 15 | Oesophagus | normal | no changes | no changes | no changes |
| 16 | Stomach | normal | no changes | no changes | no changes |
| 17 | Duodenum | normal | no changes | no changes | no changes |
| 18 | Jejunum | normal | no changes | no changes | no changes |
| 19 | Terminal ileum | normal | no changes | no changes | no changes |
| 20 | Colon | normal | no changes | no changes | no changes |
| 21 | (Rectum) | normal | no changes | no changes | no changes |
| 22 | Liver* g/100 g b. wt. | 8.79±0.07 | 9.00±0.11 p>0.05 | 9.16±0.10 p>0.05 | 8.93±0.09 p>0.05 |
| 23 | Kidney* g/100 g b. wt. | 2.39±0.12 | 2.42±0.10 p>0.05 | 2.55±0.13 p>0.05 | 2.64±0.14 p>0.05 |
| 24 | Urinary bladder | normal | no changes | no changes | no changes |
| 25 | Epididymis* g/100 g b. wt. | 0.31±0.06 | 0.28±0.05 p>0.05 | 0.33±0.07 p>0.05 | 0.37±0.08 p>0.05 |
| 26 | Testis* g/100 g b. wt. | 0.83±0.06 | 0.75±0.05 p>0.05 | 0.87±0.06 p>0.05 | 0.88±0.07 p>0.05 |
| 27 | Ovary | normal | no changes | no changes | no changes |
| 28 | Uterus | normal | no changes | no changes | no changes |
| 29 | Skin | normal | no changes | no changes | no changes |
| 30 | Mammary gland | normal | no changes | no changes | no changes |
| 31 | Mesenteric lymph node | normal | no changes | no changes | no changes |
| 32 | Skeletal muscle | normal | no changes | no changes | no changes |

Remark: * – Organs marked with an asterisk should be weighed. () – Organs listed in parenthesis should be examined if indicated by the nature of the drug or observed effects. p – Level of reliability of various parameters corresponding to control group. n – Number of rats in the groups.

FIG. 8 Results of Single-dose Toxicity studies in rats after intravenous fetal progenitor cells injections: Organs Gross Pathology

| No | Laboratory parameters | Control Group n=20 | Dose 1 n=23 | Dose 2 n=23 | Dose 3 n=30 |
|---|---|---|---|---|---|
| | Haematological Parameters | | | | |
| 1 | Haemoglobin Count, g/dl | 15.00±0.91 | 14.63±0.79 $p>0.05$ | 15.33±0.75 $p>0.05$ | 16.21±0.84 $p>0.05$ |
| 2 | Total RBC Count, $10^6/\mu l$ | 9.62±0.76 | 9.88±0.93 $p>0.05$ | 10.14±0.99 $p>0.05$ | 9.75±0.83 $p>0.05$ |
| 3 | Haematocrit, % | 45.13±1.36 | 46.71±1.57 $p>0.05$ | 48.32±1.98 $p>0.05$ | 45.95±1.58 $p>0.05$ |
| 4 | Total WBC Count, $10^3/\mu l$ | 9.39±0.81 | 8.90±0.57 $p>0.05$ | 10.00±0.90 $p>0.05$ | 9.94±0.88 $p>0.05$ |
| 5 | Differential WBC Count (%): | | | | |
| | Eosinophils | 1.36±0.38 | 1.30±0.35 $p>0.05$ | 1.38±0.27 $p>0.05$ | 1.22±0.20 $p>0.05$ |
| | Basophils | 0.28±0.19 | 0.30±0.20 $p>0.05$ | 0.32±0.18 $p>0.05$ | 0.29±0.19 $p>0.05$ |
| | Neutrophils | 47.03±2.19 | 45.98±2.00 $p>0.05$ | 46.14±1.98 $p>0.05$ | 46.02±2.00 $p>0.05$ |
| | Lymphocytes | 48.25±1.96 | 47.82±2.16 $p>0.05$ | 48.00±2.10 $p>0.05$ | 47.96±1.39 $p>0.05$ |
| | Monocytes | 3.98±0.35 | 4.60±0.52 $p>0.05$ | 4.16±0.46 $p>0.05$ | 4.51±0.54 $p>0.05$ |
| 6 | Platelet Count, $10^5/\mu l$ | 3.35±0.29 | 3.08±0.18 $p>0.05$ | 3.44±0.30 $p>0.05$ | 3.11±0.22 $p>0.05$ |
| 7 | Terminal Bone Marrow Examination | No mortality was observed. Bone marrow examination ref: "Blood SystemToxicity" | | | |
| 8 | ESR, mm/h | 7.39±0.45 | 6.97±0.26 $p>0.05$ | 7.21±0.36 $p>0.05$ | 7.65±0.30 $p>0.05$ |
| 9 | General Blood Picture | Abnormal and immature cells not detected | | | |
| | Coagulation Parameters | | | | |
| 10 | Coagulation Time, sec | 234.10±19.32 | 222.50±16.08 $p>0.05$ | 247.40±13.50 $p>0.05$ | 218.20±17.43 $p>0.05$ |
| 11 | Prothrombin Time, sec | 13.26±0.45 | 12.98±0.35 $p>0.05$ | 11.97±0.49 $p>0.05$ | 12.35±0.41 $p>0.05$ |
| 12 | Activated Partial Thromboplastin Time, sec | 30.34±1.25 | 29.52±2.02 $p>0.05$ | 34.18±1.44 $p>0.05$ | 31.51±1.40 $p>0.05$ |
| | Urinalysis Parameters | | | | |
| 13 | Colour | light-brown | light-brown | light-brown | light-brown |
| 14 | Appearance | transparent | transparent | transparent | transparent |
| 15 | Osmolity, mocmol/l | 1530.9±102.6 | 1478.5±119.1 $p>0.05$ | 1497.2±134.9 $p>0.05$ | 1508.6±135.5 $p>0.05$ |

FIG. 9 Results of Single-dose Toxicity studies in rats after intravenous fetal progenitor cells injections: haematological, coagulation, urinalysis parameters, and blood biochemical parameters

| 16 | 24-hour urinary output, ml | 3.61±0.32 | 3.48±0.29<br>p>0.05 | 3.57±0.34<br>p>0.05 | 3.70±0.38<br>p>0.05 |
|---|---|---|---|---|---|
| 17 | Reaction (pH) | 5.00±0.29 | 5.14±0.10<br>p>0.05 | 4.96±0.30<br>p>0.05 | 5.02±0.23<br>p>0.05 |
| 18 | Albumin | trace | trace | trace | trace |
| 19 | Sugar | negative | negative | negative | negative |
| 20 | Acetone | negative | negative | negative | negative |
| 21 | Bile pigments | negative | negative | negative | negative |
| 22 | Urobilinogen | negative | negative | negative | negative |
| 23 | Occult Blood | negative | negative | negative | negative |
| 24 | Microscopic examination of urinary sediment | colspan="4" No signs of pathology were observed |
| Blood Biochemical Parameters | | | | | |
| 25 | Glucose, mg/dl | 98.45±3.72 | 103.65±4.32<br>p>0.05 | 100.94±5.00<br>p>0.05 | 99.86±3.61<br>p>0.05 |
| 26 | Cholesterol, mg/dl | 43.12±2.15 | 39.98±1.75<br>p>0.05 | 40.86±1.93<br>p>0.05 | 38.88±1.76<br>p>0.05 |
| 27 | Triglycerides, mg/dl | 65.27±3.50 | 73.98±3.63<br>p>0.05 | 67.08±2.81<br>p>0.05 | 69.90±2.70<br>p>0.05 |
| 28 | Bilirubin, mg/dl | 0.64±0.10 | 0.72±0.15<br>p>0.05 | 0.71±0.12<br>p>0.05 | 0.68±0.09<br>p>0.05 |
| 29 | SGPT (ALT), IU/l | 58.72±3.32 | 55.41±3.36<br>p>0.05 | 63.10±4.27<br>p>0.05 | 56.29±3.77<br>p>0.05 |
| 30 | SGOT (AST), IU/l | 80.32±5.48 | 77.49±4.98<br>p>0.05 | 82.20±5.13<br>p>0.05 | 75.83±5.62<br>p>0.05 |
| 31 | Alkaline Phosphatase (ALP), IU/l | 230.54±8.15 | 216.51±5.95<br>p>0.05 | 240.30±7.85<br>p>0.05 | 228.93±6.86<br>p>0.05 |
| 32 | Blood Urea Nitrogen, mg/ml | 34.18±1.98 | 32.35±1.26<br>p>0.05 | 36.10±1.57<br>p>0.05 | 30.96±1.69<br>p>0.05 |
| 33 | Creatinine, mg/dl | 0.83±0.11 | 0.78±0.09<br>p>0.05 | 0.82±0.06<br>p>0.05 | 0.77±0.07<br>p>0.05 |
| 34 | Total Proteins, gm/dl | 7.50±0.57 | 6.98±0.35<br>p>0.05 | 7.12±0.30<br>p>0.05 | 7.38±0.39<br>p>0.05 |
| 35 | Albumin, gm/dl | 3.52±0.19 | 3.62±0.18<br>p>0.05 | 3.48±0.16<br>p>0.05 | 3.54±0.19<br>p>0.05 |
| 36 | Globulin, gm/dl | 3.98±0.44 | 3.36±0.31<br>p>0.05 | 3.64±0.25<br>p>0.05 | 3.84±0.26<br>p>0.05 |
| 37 | Sodium, mmol/l | 147.84±1.83 | 149.10±1.17<br>p>0.05 | 146.25±1.08<br>p>0.05 | 150.00±1.28<br>p>0.05 |
| 38 | Potassium, mmol/l | 4.16±0.19 | 4.06±0.18<br>p>0.05 | 4.29±0.21<br>p>0.05 | 4.10±0.14<br>p>0.05 |

FIG. 9 (Continued)

| 39 | Phosphorus, mg/dl | 7.77±0.45 | 8.12±0.36 p>0.05 | 7.60±0.33 p>0.05 | 8.09±0.40 p>0.05 |
| --- | --- | --- | --- | --- | --- |
| 40 | Calcium, mg/dl | 11.52±0.38 | 12.13±0.46 p>0.05 | 10.98±0.54 p>0.05 | 11.28±0.42 p>0.05 |

*Remarks:* p – level of reliability of various parameters corresponding to control group, n – number of rats in the groups

FIG. 9 (Continued)

| Group | TCA × $10^6$ | Spl × $10^6$ | Lg × $10^6$ | Cor × $10^5$ | Ren × $10^6$ | Sr × $10^5$ | Il × $10^5$ | Th × $10^5$ | Hp × $10^6$ | Number of mices in group | | Route of administration | Study duration days |
|---|---|---|---|---|---|---|---|---|---|---|---|---|---|
| | | | | | | | | | | male | female | | |
| Control group | PBS | - | - | - | - | - | - | - | - | 10 | 10 | IP | 14 |
| Dose 1 | 7.77 | 2.0 | 1.0 | 0.625 | 2.0 | 0.625 | 0.75 | 0.625 | 2.5 | 13 | 12 | IP | 14 |
| Dose 2 | 15.53 | 4.0 | 2.0 | 1.25 | 4.0 | 1.25 | 1.5 | 1.25 | 5.0 | 12 | 13 | IP | 14 |
| Dose 3 | 31.05 | 8.0 | 4.0 | 2.5 | 8.0 | 2.5 | 3.0 | 2.5 | 10.0 | 15 | 15 | IP | 14 |

Remarks: TCA – total cells amount, Spl – spleen progenitor cells, Lg – lung progenitor cells, Cor – heart progenitor cells, Ren – kidney progenitor cells, Sr – suprarenal glands progenitor cells, Il – ileum progenitor cells, Th – thymus progenitor cells, Hp – liver progenitor cells.

FIG. 10 Design of Single-dose Toxicity studies in mice after intra-peritoneum fetal progenitor cells injections

| Group | Signs of intoxication | Body weight + or – g comparison to study begining | Pathological changes of organs |
|---|---|---|---|
| Control group n=20 | No | +3.1±1.1 | No |
| Dose 1 n=25 | No | +3.0±1.2 p>0.05 | No |
| Dose 2 n=25 | No | +3.2±1.2 p>0.05 | No |
| Dose 3 n=30 | No | +3.1±1.0 p>0.05 | No |

Remark: p – level of reliability of various parameters corresponding to control group. n – number of rats in the groups.

FIG. 11 Results of Single-dose Toxicity studies in mice after intra-peritoneum fetal progenitor cells injections

| No | Organs | Control Group n=20 | Dose 1 n=25 | Dose 2 n=25 | Dose 3 n=30 |
|---|---|---|---|---|---|
| 1 | Brain* g/100 g b. wt. | 1.42±0.06 | 1.49±0.07 p>0.05 | 1.40±0.05 p>0.05 | 1.45±0.04 p>0.05 |
| 2 | (Spinal Cord) | normal | no changes | no changes | no changes |
| 3 | Eye | normal | no changes | no changes | no changes |
| 4 | (Middle Ear) | normal | no changes | no changes | no changes |
| 5 | Thyroid | normal | no changes | no changes | no changes |
| 6 | (Parathyroid) | normal | no changes | no changes | no changes |
| 7 | Spleen* g/100 g b. wt. | 0.41±0.04 | 0.40±0.03 p>0.05 | 0.38±0.04 p>0.05 | 0.42±0.05 p>0.05 |
| 8 | Thymus* g/100 g b. wt. | 0.67±0.06 | 0.62±0.05 p>0.05 | 0.69±0.06 p>0.05 | 0.71±0.05 p>0.05 |
| 9 | Adrenal* g/100 g b. wt. | 0.032±0.003 | 0.028±0.004 p>0.05 | 0.030±0.002 p>0.05 | 0.034±0.004 p>0.05 |
| 10 | (Pancreas) | normal | no changes | no changes | no changes |
| 11 | (Trachea) | normal | no changes | no changes | no changes |
| 12 | Lung* g/100 g b. wt. | 1.06±0.08 | 0.98±0.07 p>0.05 | 0.99±0.06 p>0.05 | 1.03±0.07 p>0.05 |
| 13 | Heart* g/100 g b. wt. | 0.56±0.04 | 0.50±0.04 p>0.05 | 0.54±0.05 p>0.05 | 0.56±0.03 p>0.05 |
| 14 | Aorta | normal | no changes | no changes | no changes |
| 15 | Oesophagus | normal | no changes | no changes | no changes |
| 16 | Stomach | normal | no changes | no changes | no changes |
| 17 | Duodenum | normal | no changes | no changes | no changes |
| 18 | Jejunum | normal | no changes | no changes | no changes |
| 19 | Terminal ileum | normal | no changes | no changes | no changes |
| 20 | Colon | normal | no changes | no changes | no changes |
| 21 | (Rectum) | normal | no changes | no changes | no changes |
| 22 | Liver* g/100 g b. wt. | 5.61±0.20 | 5.48±0.18 p>0.05 | 5.74±0.22 p>0.05 | 5.54±0.19 p>0.05 |
| 23 | Kidney* g/100 g b. wt. | 1.04±0.07 | 1.10±0.08 p>0.05 | 0.99±0.04 p>0.05 | 1.07±0.07 p>0.05 |
| 24 | Urinary bladder | normal | no changes | no changes | no changes |
| 25 | Epididymis* | 0.14±0.02 | 0.12±0.02 p>0.05 | 0.13±0.03 p>0.05 | 0.15±0.04 p>0.05 |
| 26 | Testis* g/100 g b. wt. | 0.45±0.04 | 0.40±0.03 p>0.05 | 0.38±0.05 p>0.05 | 0.49±0.04 p>0.05 |
| 27 | Ovary | normal | no changes | no changes | no changes |
| 28 | Uterus* g/100 g b. wt. | 0.41±0.05 | 0.38±0.03 p>0.05 | 0.40±0.04 p>0.05 | 0.43±0.03 p>0.05 |
| 29 | Skin | normal | no changes | no changes | no changes |
| 30 | Mammary gland | normal | no changes | no changes | no changes |
| 31 | Mesenteric lymph node | normal | no changes | no changes | no changes |
| 32 | Skeletal muscle | normal | no changes | no changes | no changes |

*Remarks*: * -- Organs marked with an asterisk should be weighed. () -- Organs listed in parenthesis should be examined if indicated by the nature of the drug or observed effects. p -- Level of reliability of various parameters corresponding to control group. n -- Number of mices in the groups.

FIG. 12 Results of Single-dose Toxicity studies in mice after intra-peritoneum fetal progenitor cells injections: Organs Gross Pathology

| No | Laboratory parameters | Control Group n=20 | Dose 1 n=25 | Dose 2 n=25 | Dose 3 n=30 |
|---|---|---|---|---|---|
| | | Haematological Parameters | | | |
| 1 | Haemoglobin Count, g/dl | 9.98±0.35 | 10.26±0.48 p>0.05 | 9.74±0.53 p>0.05 | 11.09±0.61 p>0.05 |
| 2 | Total RBC Count, $10^6/\mu l$ | 7.18±0.38 | 7.00±0.26 p>0.05 | 6.98±0.31 p>0.05 | 7.27±0.22 p>0.05 |
| 3 | Haematocrit, % | 35.21±1.54 | 33.92±1.29 p>0.05 | 32.98±1.63 p>0.05 | 36.12±1.69 p>0.05 |
| 4 | Total WBC Count, $10^3/\mu l$ | 20.42±1.85 | 19.89±1.21 p>0.05 | 18.95±1.37 p>0.05 | 22.16±1.94 p>0.05 |
| 5 | Differential WBC Count (%): | | | | |
| | Granulocytes | 9.89±0.78 | 9.45±0.92 p>0.05 | 9.80±0.85 p>0.05 | 10.12±0.99 p>0.05 |
| | Lymphocytes | 72.36±1.95 | 73.82±1.15 p>0.05 | 73.98±1.90 p>0.05 | 71.60±1.21 p>0.05 |
| | Monocytes | 14.53±0.89 | 13.00±0.73 p>0.05 | 12.97±0.52 p>0.05 | 14.66±0.79 p>0.05 |
| 6 | Platelet Count, $10^5/\mu l$ | 3.22±0.11 | 3.73±0.19 p>0.05 | 3.25±0.15 p>0.05 | 3.62±0.18 p>0.05 |
| 7 | Terminal Bone Marrow Examination | No mortality was observed. | | | |
| 8 | General Blood Picture | Abnormal and immature cells not detected | | | |
| | | Coagulation Parameters | | | |
| 9 | Bleeding Time, min | 3.49±0.19 | 3.51±0.20 p>0.05 | 3.32±0.17 p>0.05 | 3.68±0.18 p>0.05 |
| 10 | Coagulation Time, min | 2.12±0.12 | 2.18±0.11 p>0.05 | 1.97±0.10 p>0.05 | 2.24±0.09 p>0.05 |
| | | Urinalysis Parameters | | | |
| 11 | Colour | dark-brown | dark-brown | dark-brown | dark-brown |
| 12 | Appearance | transparent | transparent | transparent | transparent |
| 13 | Osmolity, mocmol/l | 1486.3±75.4 | 1398.5±65.3 p>0.05 | 1432.7±73.9 p>0.05 | 1505.4±80.6 p>0.05 |
| 14 | 24-hour urinary output, ml | 0.65±0.04 | 0.60±0.05 p>0.05 | 0.58±0.07 p>0.05 | 0.59±0.06 p>0.05 |
| 15 | Reaction (pH) | 4.80±0.04 | 4.82±0.03 p>0.05 | 4.72±0.05 p>0.05 | 4.76±0.03 p>0.05 |
| 16 | Albumin | trace | trace | trace | trace |
| 17 | Sugar | negative | negative | negative | negative |
| 18 | Acetone | negative | negative | negative | negative |
| 19 | Bile pigments | negative | negative | negative | negative |
| 20 | Urobilinogen | negative | negative | negative | negative |
| 21 | Occult Blood | negative | negative | negative | negative |
| 22 | Microscopic examination of urinary sediment | No signs of pathology were observed | | | |

FIG. 13 Results of Single-dose Toxicity studies in mice after intra-peritoneum fetal progenitor cells administration: haematological, coagulation, urinalysis parameters, and blood biochemical parameters

| | | Blood Biochemical Parameters | | | |
|---|---|---|---|---|---|
| 23 | Glucose, mg/dl | 139.72±5.72 | 142.16±6.39 $p>0.05$ | 145.48±5.81 $p>0.05$ | 136.44±4.23 $p>0.05$ |
| 24 | Cholesterol, mg/dl | 77.53±3.50 | 81.65±4.22 $p>0.05$ | 79.20±4.04 $p>0.05$ | 82.08±4.95 $p>0.05$ |
| 25 | Triglycerides, mg/dl | 87.67±4.60 | 91.65±4.89 $p>0.05$ | 85.47±4.25 $p>0.05$ | 92.13±4.98 $p>0.05$ |
| 26 | Bilirubin, mg/dl | 0.50±0.04 | 0.47±0.03 $p>0.05$ | 0.53±0.05 $p>0.05$ | 0.49±0.04 $p>0.05$ |
| 27 | SGPT (ALT), IU/l | 42.03±3.38 | 36.19±2.96 $p>0.05$ | 44.73±2.72 $p>0.05$ | 39.94±2.90 $p>0.05$ |
| 28 | SGOT (AST), IU/l | 135.74±7.42 | 126.98±5.16 $p>0.05$ | 140.10±7.30 $p>0.05$ | 125.36±4.26 $p>0.05$ |
| 29 | Alkaline Phosphatase (ALP) IU/l | 498.62±23.17 | 549.75±25.96 $p>0.05$ | 533.12±26.50 $p>0.05$ | 507.05±24.58 $p>0.05$ |
| 30 | Blood Urea Nitrogen, mg/dl | 20.57±1.64 | 18.90±1.49 $p>0.05$ | 23.16±1.57 $p>0.05$ | 24.92±1.92 $p>0.05$ |
| 31 | Creatinine, μmol/l | 53.44±4.72 | 45.16±2.96 $p>0.05$ | 49.23±2.48 $p>0.05$ | 47.92±2.56 $p>0.05$ |
| 32 | Total Proteins, g/dl | 6.90±0.39 | 6.56±0.41 $p>0.7$ | 7.08±0.25 $p>0.5$ | 7.11±0.46 $p>0.4$ |
| 33 | Albumin, g/dl | 2.92±0.12 | 2.87±0.11 $p>0.05$ | 3.04±0.13 $p>0.05$ | 3.06±0.14 $p>0.05$ |
| 34 | Globulin, g/dl | 3.98±0.20 | 3.69±0.18 $p>0.05$ | 4.04±0.21 $p>0.05$ | 4.05±0.22 $p>0.05$ |
| 35 | Sodium, mmol/l | 151.60±1.52 | 148.19±1.47 $p>0.05$ | 147.93±1.39 $p>0.05$ | 149.88±1.44 $p>0.05$ |
| 36 | Potassium, mmol/l | 4.91±0.21 | 4.86±0.17 $p>0.05$ | 4.85±0.12 $p>0.05$ | 4.95±0.14 $p>0.05$ |
| 37 | Phosphorus, mg/dl | 6.96±0.34 | 7.31±0.35 $p>0.05$ | 7.08±0.32 $p>0.05$ | 7.57±0.39 $p>0.05$ |
| 38 | Calcium, mg/dl | 11.28±0.61 | 9.86±0.54 $p>0.05$ | 10.69±0.53 $p>0.05$ | 11.90±0.65 $p>0.05$ |

Remarks: p – Level of reliability of various parameters corresponding to control group. n – Number of mices in the groups FIG. 13 (Continued)

| Study parameters | Control n=14 | Fetal progenitor cells transplantation *group 1* n=14 | Fetal progenitor cells transplantation *group 2* n=14 |
|---|---|---|---|
| Quantity of leukocytes, G/l | 7.21±0.42 | 7.19±0.80 $p>0.9$ | 7.92±0.77 $p>0.4$ $p_1>0.5$ |
| Eosinophils, % | 1.21±0.36 | 1.36±0.50 $p>0.8$ | 1.57±0.47 $p>0.5$ $p_1>0.7$ |
| Basophils, % | 0.50±0.25 | 0.14±0.10 $p>0.1$ | 0.29±0.13 $p>0.4$ $p_1>0.1$ |
| Metamyelocytes, % | 0±0 | 0.14±0.14 | 0.50±0.23 $p_1>0.1$ |
| Band neutrophils, % | 3.86±0.52 | 6.07±1.41 $p>0.1$ | 4.21±0.74 $p>0.7$ $p_1>0.2$ |
| Segmented neutrophils, % | 42.43±1.55 | 41.29±1.84 $p>0.6$ | 40.43±2.83 $p>0.5$ $p_1>0.8$ |
| Lymphocytes (total quantity), % | 47.50±3.42 | 46.50±2.28 $p>0.7$ | 47.57±4.14 $p>0.9$ $p_1>0.8$ |
| Lymphocytes small, % | 37.79±3.90 | 38.36±2.60 $p>0.6$ | 38.86±4.27 $p>0.8$ $p_1>0.7$ |
| Lymphocytes moderate, % | 5.36±0.64 | 4.57±0.43 $p>0.3$ | 5.00±0.70 $p>0.7$ $p_1>0.6$ |
| Lymphocytes large, % | 3.64±0.61 | 3.57±0.95 $p>0.9$ | 3.71±0.62 $p>0.9$ $p_1>0.9$ |
| Monocytes, % | 4.50±0.56 | 4.71±0.74 $p>0.8$ | 6.71±1.01 $p>0.06$ $p_1>0.1$ |

*Remarks:* p – level of reliability of various parameters corresponding to control; $p_1$ – level of reliability of various parameters in animals of first and second group; n – Number of rats in the groups.

FIG. 14 Influence of human fetal progenitor cells transplantation on the quantity of leukocytes and leukocytes blood formula in Wistar rats

| Study parameters | Control n=14 | Fetal progenitor cells transplantation group 1 n=14 | Fetal progenitor cells transplantation group 2 n=14 |
|---|---|---|---|
| Eosinophils, Quantity in 1 µl of blood | 55.9±33.6 | 55.71±16.52 p>0.9 | 105.9±31.56 p>0.2 $p_1$>0.1 |
| Basophils, Quantity in 1 µl of blood | 21.8±21.8 | 10.86±8.76 p>0.6 | 21.21±9.58 p>0.9 $p_1$>0.4 |
| Metamyelocytes, Quantity in 1 µl of blood | 0±0 | 13.36±10.51 | 28.43±13.63 $p_1$>0.3 |
| Band-nucleus neutrophils, Thousand/1 µl of blood | 289.30±50.51 | 565.20±133.70 p>0.06 | 277.4±41.65 p>0.8 $p_1$>0.05 |
| Segmented-nucleus neutrophils, Thousand/1 µl of blood | 3070.0±228.7 | 2879.0±357.00 p>0.6 | 2748.0±252.1 p>0.3 $p_1$>0.7 |
| Lymphocytes (Total quantity), Thousand/1 µl of blood | 3420.0±243.3 | 3124.0±389.2 p>0.5 | 3504.0±538.8 p>0.8 $p_1$>0.5 |
| Lymphocytes small, Thousand/1 µl of blood | 2714.0±237.4 | 2676.0±347.2 p>0.9 | 2867.0±508.9 p>0.7 $p_1$>0.7 |
| Lymphocytes moderate, Thousand/1 µl of blood | 397.70±60.68 | 328.60±47.38 p>0.3 | 364.90±50.17 p>0.6 $p_1$>0.6 |
| Lymphocytes large, Thousand/1 µl of blood | 258.80±45.06 | 246.90±76.20 p>0.8 | 272.01±34.72 p>0.8 $p_1$>0.7 |
| Monocytes, Thousand/1 µl of blood | 331.50±55.16 | 289.50±60.48 p>0.6 | 433.40±75.75 p>0.2 $p_1$>0.1 |

*Remark:* p – level of reliability of various parameters corresponding to control; $p_1$ – level of reliability of various parameters in animals of first and second group; n – number of rats in the groups.

FIG. 15 Influence of human fetal progenitor cells transplantation on absolute quantity of leukocytes in peripheral blood of Wistar rats

| Study parameters | Control n=14 | Fetal progenitor cells transplantation group 1 n=14 | Fetal progenitor cells transplantation group 2 n=14 |
|---|---|---|---|
| Blasts, % | 0.050±0.027 | 0.154±0.060 p>0.1 | 0.125±0.057 p>0.2 $p_1$>0.7 |
| Promyelocytes, % | 0.329±0.084 | 0.496±0.086 p>0.1 | 0.321±0.082 p>0.9 $p_1$>0.1 |
| Myelocytes, % | 8.02±0.54 | 7.25±0.46 p>0.2 | 6.64±0.60 p>0.09 $p_1$>0.4 |
| Metamyelocytes, % | 3.96±0.53 | 3.16±0.43 p>0.2 | 3.57±0.25 p>0.5 $p_1$>0.4 |
| Band-nucleus neutrophils, % | 11.45±0.79 | 11.43±1.03 p>0.9 | 9.78±0.90 p>0.1 $p_1$>0.2 |
| Segmented-nucleus neutrophils, % | 11.77±0.83 | 11.57±1.12 p>0.8 | 11.83±1.71 p>0.9 $p_1$>0.8 |
| Eosinophils, % | 9.84±0.98 | 8.28±1.05 p>0.2 | 10.50±1.30 p>0.6 $p_1$>0.1 |
| Basophils (mastocytes), % | 0.264±0.071 | 0.192±0.044 p>0.3 | 0.333±0.076 p>0.5 $p_1$>0.1 |
| Monocytes, % | 0.225±0.144 | 0.092±0.052 p>0.3 | 0.092±0.054 p>0.3 $p_1$>0.9 |
| Lymphocytes, % | 17.30±0.77 | 15.95±1.11 p>0.3 | 19.06±1.54 p>0.3 $p_1$>0.1 |
| Plasmatic cells, % | 1.57±0.24 | 1.68±0.32 p>0.7 | 1.75±0.34 p>0.6 $p_1$>0.8 |
| Megakaryocytes, % | 0.161±0.036 | 0.196±0.035 p>0.4 | 0.217±0.059 p>0.4 $p_1$>0.7 |

FIG. 16 Influence of human progenitor cells transplantation on parameters of myelograms in Wistar rats

| Erythroblasts, % | 0.08±0.04 | 0.79±0.69<br>p>0.3 | 0.03±0.02<br>p>0.2<br>p₁>0.2 |
|---|---|---|---|
| Pronormocytes, % | 0.59±0.12 | 0.74±0.13<br>p>0.4 | 0.41±0.09<br>p>0.2<br>p₁<0.05 |
| Normocytes basophilic, % | 17.05±0.73 | 14.03±1.36<br>p>0.06 | 11.92±1.19<br>p<0.01<br>p₁>0.2 |
| Normocytes polychromatophilic, % | 15.31±1.02 | 21.32±1.34<br>p<0.01 | 21.27±0.92<br>p<0.001<br>p₁>0.9 |
| Normocytes oxyphilic, % | 1.55±0.25 | 2.50±0.29<br>p<0.05 | 3.15±0.63<br>p<0.05<br>p₁>0.3 |
| Coefficient ratio of lymphoid and erythrocytes germs, units | 1.96±0.12 | 1.60±0.08<br>p<0.02 | 1.79±0.15<br>p>0.3<br>p₁>0.2 |
| Index stimulation of neutrophilogenesis, units | 0.55±0.07 | 0.49±0.05<br>p>0.4 | 0.51±0.08<br>p>0.7<br>p₁>0.8 |
| Plasmoblasts, % | 0±0 | 0±0 | 0±0 |

Remarks: p – level of reliability of various parameters corresponding to control; p₁ – level of reliability of various parameters in animals of first and second group; n – number of rats in the groups.

FIG. 16 (Continued)

| Study parameters | Control n=14 | Fetal progenitor cells transplantation group 1 n=14 | Fetal progenitor cells transplantation group 2 n=14 |
|---|---|---|---|
| *Peripheral blood* | | | |
| Quantity of erythrocytes, T/l | 5.76±0.26 | 6.23±0.18 $p>0.1$ | 6.70±0.41 $p>0.06$ $p_1>0.3$ |
| Hemoglobin, g/l | 129.30±1.80 | 149.90±2.29 $p<0.001$ | 157.40±5.84 $p<0.001$ $p_1>0.2$ |
| Color parameters, units | 0.70±0.04 | 0.73±0.03 $p>0.5$ | 0.73±0.04 $p>0.5$ $p_1>0.9$ |
| Erythrocytes sedimentation rate, mm per 2 hours | 2.43±0.34 | 1.40±0.21 $p<0.02$ | 1.60±0.20 $p<0.05$ $p_1>0.4$ |
| *Bone marrow* | | | |
| Erythroblasts, % | 0.29±0.13 | 0.35±0.13 $p>0.7$ | 0.13±0.09 $p>0.3$ $p_1>0.1$ |
| Pronormocytes, % | 1.32±0.31 | 1.73±0.42 $p>0.4$ | 1.08±0.27 $p>0.5$ $p_1>0.2$ |
| Normocytes basophilic, % | 49.00±1.24 | 37.38±2.17 $p<0.001$ | 31.75±2.42 $p<0.001$ $p_1>0.09$ |
| Normocytes polychromatophilic, % | 45.04±1.61 | 54.31±2.27 $p<0.01$ | 58.54±2.12 $p<0.001$ $p_1>0.1$ |
| Normocytes oxyphilic, % | 4.36±0.82 | 6.23±0.80 $p>0.1$ | 8.50±1.30 $p<0.02$ $p_1<0.05$ |
| Index stimulation of erythropoiesis, units | 0.49±0.01 | 0.59±0.02 $p<0.001$ | 0.68±0.02 $p<0.001$ $p_1<0.01$ |

*Remarks:* p -- level of reliability of various parameters corresponding to control; $p_1$ -- level of reliability of various parameters in animals of first and second group; n -- number of rats in the groups

FIG. 17 Influence of human fetal progenitor cells transplantation on erythron of Wistar rats

| Animals group | Study parameters | Period of surveillance, Days | | | | | | |
|---|---|---|---|---|---|---|---|---|
| | | 0 | 6 | 12 | 18 | 60 | 120 |
| Introduction of busulfan and 0.9% of sodium chloride, n=15 1 group | Quantity of mononuclear cells in bone marrow, × 10⁹/l | 39.17±1.65 | 27.10±2.59 p<0.001 | 30.17±2.18 p<0.01 | 27.00±2.44 p<0.001 | 32.67±2.06 p<0.05 | 34.40±2.15 p>0.08 |
| | Contents of reticulocytes in bone marrow, % | 3.53±0.15 | 1.48±0.16 p<0.001 | 1.55±0.24 p<0.001 | 1.58±0.19 p<0.001 | 1.97±0.21 p<0.001 | 2.66±0.18 p<0.001 |
| | Contents of fetal hemoglobin in blood, % | 0.69±0.08 | 0.70±0.07 p>0.9 | 0.72±0.06 p>0.7 | 0.65±0.04 p>0.6 | 0.49±0.05 p<0.05 | 0.38±0.04 p<0.01 |
| Introduction of busulfan and human fetal progenitor cells transplantation, n=15 2 group | Quantity of mononuclear cells in bone marrow, × 10⁹/l | 40.12±1.82 $p_1$>0.7 | 28.15±2.46 p<0.001 $p_1$>0.7 | 32.94±2.35 p<0.05 $p_1$>0.4 | 31.29±2.56 p<0.01 $p_1$>0.2 | 45.50±3.63 p>0.1 $p_1$<0.01 | 43.71±3.88 p>0.4 $p_1$<0.05 |
| | Contents of reticulocytes in bone marrow, % | 3.64±0.18 $p_1$>0.6 | 1.53±0.17 p<0.001 $p_1$>0.8 | 1.70±0.22 p<0.001 $p_1$>0.6 | 1.85±0.20 p<0.001 $p_1$>0.3 | 3.10±0.26 p>0.09 $p_1$<0.01 | 4.92±0.21 p<0.001 $p_1$<0.001 |
| | Contents of fetal hemoglobin in blood, % | 0.74±0.09 $p_1$>0.6 | 3.29±0.46 p<0.001 $p_1$<0.001 | 4.31±0.38 p<0.001 $p_1$<0.001 | 9.10±0.78 p<0.001 $p_1$<0.001 | 28.05±1.66 p<0.001 $p_1$<0.001 | 23.89±1.92 p<0.001 $p_1$<0.001 |

Remarks: 0 — initial parameters; p — level of reliability of various parameters corresponding to initial parameters; $p_1$ — level of reliability of various parameters in experimental groups; n — number of animals in experiments.

FIG. 18 Dynamics of the contents of mononuclear cells in bone marrow, reticulocytes and human fetal hemoglobin in blood of immunosuppressed rabbits after human progenitor cells transplantation

| PO (day) | Hb g/l | RBC T/l | RC % | TC G/l | WBC G/l | Neutrophils, % | | | BF % | EF % | LC % | MC % |
|---|---|---|---|---|---|---|---|---|---|---|---|---|
| | | | | | | Yo-N | St-N | Seg-N | | | | |
| 0 | 124.5±3.2 | 6.10±0.26 | 3.50±0.19 | 217.5±6.44 | 9.20±0.17 | 0.50±0.20 | 3.50±0.29 | 46.30±1.30 | 3.25±0.48 | 1.25±0.14 | 41.00±2.31 | 4.20±0.22 |
| 6 | 118.5±2.0 p>0.1 | 4.80±0.18 p<0.001 | 0.92±0.06 p<0.001 | 110.0±5.93 p<0.001 | 4.60±0.69 p<0.001 | 0±0 | 11.75±0.91 p<0.001 | 56.00±2.31 p<0.01 | 3.25±0.36 p>0.9 | 0.75±0.09 p<0.01 | 26.80±2.01 p<0.001 | 1.45±0.25 p<0.001 |
| 12 | 104.0±3.5 p<0.001 | 4.10±0.12 p<0.001 | 0.98±0.10 p<0.001 | 108.0±5.39 p<0.001 | 4.33±0.23 p<0.001 | 0.25±0.14 p>0.3 | 12.25±1.43 p<0.001 | 50.45±2.73 p>0.1 | 2.50±0.29 p>0.1 | 1.25±0.10 p>0.9 | 30.30±2.37 p<0.01 | 2.50±0.23 p<0.001 |
| 18 | 108.5±2.9 p<0.001 | 5.15±0.23 p<0.02 | 1.30±0.09 p<0.001 | 109.0±5.20 p<0.001 | 5.30±0.35 p<0.001 | 0±0 | 4.50±0.36 p<0.05 | 60.50±2.94 p<0.001 | 2.50±0.31 p>0.2 | 0.75±0.07 p<0.01 | 29.50±2.45 p<0.01 | 2.25±0.19 p<0.001 |
| 60 | 116.0±5.2 p>0.1 | 6.15±0.26 p>0.08 | 2.62±0.15 p<0.01 | 176.5±7.93 p<0.001 | 5.80±0.26 p<0.001 | 0.50±0.16 p>0.9 | 6.25±0.38 p<0.001 | 53.00±1.58 p<0.01 | 2.50±0.24 p>0.1 | 1.00±0.20 p>0.3 | 33.50±1.79 p>0.02 | 3.25±0.27 p<0.02 |
| 120 | 130.0±2.7 p>0.1 | 6.40±0.11 p>0.2 | 3.89±0.30 p>0.3 | 223.0±8.52 p>0.6 | 7.95±0.38 p<0.01 | 0.50±0.11 p>0.9 | 3.00±0.37 p>0.2 | 48.95±2.10 p>0.2 | 1.50±0.09 p<0.01 | 1.00±0.16 p>0.2 | 40.80±3.33 p>0.9 | 4.25±0.40 p>0.9 |

Remarks: PO – period of observance; Hb – hemoglobin, RBC – red blood cells, RC – reticulocytes, TC – thrombocytes, WBC – white blood cells, Yo-N – metamyelocytes, St-N – band-nucleus neutrophils, Seg-N – segmented-nucleus neutrophils, BF – basophilic leucocytes, EF – eosinophilic leucocytes, LC – lymphocytes, MC – monocytes; 0 – initial parameters (control); p – level of reliability in various parameters corresponding to control; n – number of animals in experiments FIG. 19 Dynamics changes of parameters in blood of immunosuppressed rabbits (n=15) after human fetal progenitor cells transplantation

| PO (day) | Neutrophils per 1 μl | | | BF per 1 μl | EF per 1 μl | LC per 1 μl | MC per 1 μl |
|---|---|---|---|---|---|---|---|
| | Yo-N | St-N | Seg-N | | | | |
| 0 | 46.0±18.4 | 322.0±26.7 | 4259.6±119.6 | 299.0±44.2 | 115.0±12.9 | 3772.0±212.5 | 386.4±20.2 |
| 6 | 0±0 | 540.5±41.9 p<0.001 | 2576.0±106.3 p<0.001 | 149.5±16.6 p<0.01 | 34.5±4.1 p<0.001 | 1232.8±92.5 p<0.001 | 66.7±11.5 p<0.001 |
| 12 | 10.8±6.1 p>0.07 | 530.4±61.9 p<0.01 | 2184.5±118.2 p<0.001 | 108.3±12.6 p<0.001 | 54.1±4.3 p<0.001 | 1312.0±102.6 p<0.001 | 108.3±10.0 p<0.001 |
| 18 | 0±0 | 238.5±19.1 p<0.02 | 3206.5±155.8 p<0.001 | 132.5±16.4 p<0.01 | 39.8±3.7 p<0.001 | 1563.5±129.9 p<0.001 | 119.3±10.1 p<0.001 |
| 60 | 29.0±9.3 p>0.4 | 362.5±22.0 p>0.2 | 3074.0±91.6 p<0.001 | 145.0±13.9 p<0.01 | 58.0±11.6 p<0.01 | 1943.0±103.8 p<0.001 | 188.5±15.7 p<0.001 |
| 120 | 39.8±8.7 p>0.7 | 238.5±29.4 p<0.05 | 3891.5±167.0 p>0.08 | 119.3±7.2 p<0.001 | 79.5±12.7 p>0.5 | 3243.6±264.7 p>0.3 | 337.9±31.8 p>0.2 |

Remarks: PO – Period of observance; WBC – white blood cells, Yo-N – metamyelocytes, St-N – band-nucleus neutrophils, Seg-N – segmented-nucleus neutrophils, BF – basophilic leukocytes, EF – eosinophilic leukocytes, LC – lymphocytes, MC – monocytes; 0 – initial parameters (control); p – level of reliability in various corresponding control; n – number of animals in experiments.

FIG. 20 Dynamics changes of absolute parameters quantity of leukocytes in blood of immunosuppressed rabbits (n=15) after human fetal progenitor cells transplantation

| Animal groups | Mass of testes | Mass of epididymises | Mass of prostate ventral part | Mass of prostate anterior part |
|---|---|---|---|---|
| Control<br>n=8 | 799.7 ± 25.4 | 274.6 ± 4.6 | 135.9 ± 7.2 | 42.1 ± 3.2 |
| Introduction of human fetal progenitor cells in intact rats, n=5<br>*1 group* | 721.7 ± 37.5<br>$p>0.1$ | 254.2 ± 12.1<br>$p>0.09$ | 130.5 ± 9.1<br>$p>0.6$ | 44.1 ± 4.3<br>$p>0.7$ |
| Introduction of busulfan, n=10<br>*2 group* | 392.1 ± 31.0<br>$p<0.001$ | 205.6 ± 7.9<br>$p<0.001$ | 119.2 ± 5.0<br>$p>0.06$ | 36.3 ± 4.1<br>$p>0.2$ |
| Introduction of busulfan and human fetal progenitor cells transplantation, n=16<br>*3 group* | 571.2 ± 27.7<br>$p<0.001$<br>$p_1<0.02$<br>$p_2<0.001$ | 221.2 ± 8.2<br>$p<0.001$<br>$p_1>0.05$<br>$p_2>0.2$ | 124.7 ± 8.2<br>$p>0.3$<br>$p_1>0.7$<br>$p_2>0.6$ | 40.6 ± 4.7<br>$p>0.8$<br>$p_1>0.6$<br>$p_2>0.5$ |
| Repeated introduction of human fetal progenitor cells in immunosuppressed rats, n=16<br>*4 group* | 795.0 ± 28.1<br>$p>0.9$<br>$p_3<0.001$ | 284.1 ± 9.3<br>$p>0.4$<br>$p_3<0.001$ | 138.8 ± 6.4<br>$p>0.7$<br>$p_3>0.1$ | 42.5 ± 2.1<br>$p>0.9$<br>$p_3>0.7$ |

*Remarks*: p – level of reliability of various parameters in comparison with control; $p_1$, $p_2$, $p_3$ – in comparison with the data corresponding groups of rats; n – number of rats in the group

FIG. 21 Influence of human fetal progenitor cells transplantation in relative mass of testes, epididymises and prostates (mg/100 g body mass) in rats Wistar

| Animal groups | Testosterone nm/ml | Biological active luteinizing hormone, MU/l |
|---|---|---|
| Control n=8 | 10.31 ± 2.75 | 4.27 ± 0.48 |
| Introduction of human fetal progenitor cells in intact rats, n=5 *1 group* | 16.90 ± 2.52 p>0.1 | 4.60 ± 0.53 p>0.6 |
| Introduction of busulfan, n=10 *2 group* | 2.54 ± 0.28 p<0.01 | 2.12 ± 0.19 p<0.001 |
| Introduction of busulfan and human fetal progenitor cells transplantation, n=16 *3 group* | 6.31 ± 1.06 p>0.1 $p_1$<0.001 $p_2$<0.02 | 3.80 ± 0.30 p>0.4 $p_1$>0.2 $p_2$<0.001 |
| Repeated introduction of human fetal progenitor cells in immunosuppressed rats, n=16 *4 group* | 13.65 ± 1.54 p>0.2 $p_3$<0.001 | 4.93 ± 0.46 p>0.5 $p_3$<0.05 |

Remarks: p – level of reliability of various parameters in comparison with control; $p_1$, $p_2$, $p_3$ – in comparison with the data corresponding groups of rats; n – number of rats in the group

FIG. 22 Influence of human fetal progenitor cells transplantation on the content in testosterone and biological active luteinizing hormone in blood plasma of the rats Wistar

| Animal groups | Activity of 3β-hydroxy-Δ⁵-steroido-dehyrogenase | |
|---|---|---|
| | *per 1 mg of protein* | *per 1 g of tissue* |
| Control<br>n=8 | 4.00 ± 0.19 | 199.78 ± 8.84 |
| Introduction of human fetal progenitor cells in intact rats,<br>n=5<br>*1 group* | 3.86 ± 0.33<br>p>0.6 | 183.89 ± 10.51<br>p>0.2 |
| Introduction of busulfan, n=10<br>*2 group* | 2.93 ± 0.22<br>p<0.01 | 143.35 ± 9.38<br>p<0.001 |
| Introduction of busulfan and human fetal progenitor cells transplantation,<br>n=16<br>*3 group* | 4.61 ± 0.31<br>p>0.2<br>$p_1$>0.2<br>$p_2$<0.001 | 213.96 ± 14.07<br>p>0.5<br>$p_1$>0.2<br>$p_2$<0.01 |
| Repeated introduction of human fetal progenitor cells in immunosuppressed rats, n=16<br>*4 group* | 5.44 ± 0.38<br>p<0.02<br>$p_3$>0.1 | 249.03 ± 15.70<br>p<0.05<br>$p_3$>0.1 |

Remarks: p – level of reliability of various parameters in comparison with control; $p_1$, $p_2$, $p_3$ – in comparison with the data corresponding groups of rats; n – number of rats in the group

FIG. 23 Influence of human fetal progenitor cells transplantation on the activity of 3β-hydroxyl-Δ⁵-steroid-dehydrogenase in testes of rats Wistar

| Animal groups | Concentration of spermatozoids, bill/ml |
|---|---|
| Control<br>n=8 | 81.4 ± 4.3 |
| Introduction of human fetal progenitor cells in intact rats,<br>n=5<br>*1 group* | 92.3 ± 5.6<br>$p>0.1$ |
| Introduction of busulfan, n=10<br>*2 group* | 39.0 ± 4.1<br>$p<0.001$ |
| Introduction of busulfan and human fetal progenitor cells transplantation, n=16<br>*3 group* | 99.5 ± 7.5<br>$p>0.1$<br>$p_1>0.6$<br>$p_2<0.001$ |
| Repeated introduction of human fetal progenitor cells in immunosuppressed rats, n=16<br>*4 group* | 117.9 ± 6.7<br>$p<0.01$<br>$p_3>0.07$ |

*Remarks*: p – level of reliability of various parameters in comparison with control; $p_1$, $p_2$, $p_3$ – in comparison with the data corresponding groups of rats; n – number of rats in the group

FIG. 24 Influence of human fetal progenitor cells transplantation on concentration of spermatozoids in epididymises of the Wistar rats

| Animal groups | Index of spermatogensis Units |
|---|---|
| Control n=8 | 3.11 ± 0.10 |
| Introduction of human fetal progenitor cells in intact rats, n=5 *1 group* | 4.20 ± 0.27 p<0.001 |
| Introduction of busulfan, n=10 *2 group* | 1.35 ± 0.10 p<0.001 |
| Introduction of busulfan and human fetal progenitor cells transplantation, n=16 *3 group* | 4.04 ± 0.15 p<0.001 $p_1$>0.6 $p_2$<0.001 |
| Repeated introduction of human fetal progenitor cells in immunosuppressed rats, n=16 *4 group* | 5.34 ± 0.09 p<0.001 $p_3$<0.001 |

*Remarks*: p – level of reliability of various parameters in comparison with control; $p_1$, $p_2$, $p_3$ – in comparison with the data corresponding groups of rats; n – number of rats in the group

FIG. 25 Influence of human fetal progenitor cells transplantation on index of spermatogenesis in testes of the rats Wistar

| Animal groups | Fructose, micromole/mg tissue |
|---|---|
| Control<br>n=8 | $0.94 \pm 0.03$ |
| Introduction of human fetal progenitor cells in intact rats,<br>n=5<br>*1 group* | $1.26 \pm 0.07$<br>$p<0.001$ |
| Introduction of busulfan, n=10<br>*2 group* | $0.70 \pm 0.04$<br>$p<0.001$ |
| Introduction of busulfan and human fetal progenitor cells transplantation, n=16<br>*3 group* | $1.08 \pm 0.08$<br>$p>0.2$<br>$p_1>0.2$<br>$p_2<0.01$ |
| Repeated introduction of human fetal progenitor cells in immunosuppressed rats, n=16<br>*4 group* | $1.77 \pm 0.09$<br>$p<0.001$<br>$p_3<0.001$ |

*Remarks*: p – level of reliability of various parameters in comparison with control; $p_1$, $p_2$, $p_3$ – in comparison with the data corresponding groups of rats; n – number of rats in the group

FIG. 26 Influence of human fetal progenitor cells transplantation on content of fructose in anterior part of prostates in the rats Wistar

FIG. 27 Human abortive placenta in 20 weeks gestation term

METHOD OF PROGENITOR CELL ISOLATION FROM DIFFERENT ORGANS BY NATURAL DESTRUCTION OF EXTRACELLULAR MATRIX

FIELD OF THE INVENTION

The present invention relates to the isolation of fetal progenitor cells from the organs of an aborted fetus after medical termination of a pregnancy, wherein said progenitor cells are available for subsequent therapeutic use.

BACKGROUND OF THE INVENTION

Progenitor cells are already more specialised than a stem cells and are restricted to differentiate into tissue-specific or organ-specific cells. The most important difference between stem cells and progenitor cells is that progenitor cells have on their surface many regulatory proteins, which provide them with primary specialization. Currently available methods for stem cells separation are inadequate and inefficient as the techniques involved in the isolation of progenitor cells. Certain methods employed for progenitor cells isolation involve destruction of extracellular matrix by collagenase and DNase. Such methodology not only causes the extracellular matrix to be damaged, it also results in the destruction of transmembrane regulatory proteins. Following such procedures, the progenitor cells are no longer intact, no longer possessing proliferative ability and importantly, the vital differentiation capacity is negatively altered.

The extracellular matrix (ECM) is a collection of extracellular molecules secreted by cells that provides structural and biochemical support to the surrounding cells. The ECM is mainly composed of an intricate interlocking mesh of fibrillar and non-fibrillar collagens, elastic fibers and glycosaminoglycan-containing non-collagenous glycoproteins (hyaluronan and proteoglycans). This tissue compartment provides structural support by maintaining organs and complex tissues. ECM of the fetus and the adult is significantly different. In the study by Coolen et al. (2010) most differences between fetal and adult skin were found in the expression pattern of ECM molecules. Both fibronectin and chondroitin sulfate were more abundantly present in the fetal dermis than in adult dermis, and elastin was not found in the fetal skin until 22 weeks of gestation [Coolen N. A., Schouten K., Middelkoop E., Ulrich M. (2010) *Arch Dermatol Res*].

As has been established by numerous studies, extensive ECM remodeling is critical in many birth-related physiological processes such as cervical ripening, fetal membrane rupture, and placental detachment [Bryant-Greenwood G D, Yamamoto S Y. (1995) *Am J Obstet Gynecol*; Draper D, McGregor J, Hall J, Jones W, Beutz M, Heine R P, et al. (1995) *Am J Obstet Gynecol*; Rajabi M R, Dean D D, Beydoun S N, Woessner Jr J F. (1988) *Am J Obstet Gynecol*; Tsatas D, Baker M S, Rice G E. (1999) *J Reprod Fertil*; Vadillo-Ortega F, Gonzalez-Avila G, Furth E E, Lei H, Muschel R J, Stetler-Stevenson W G, et al. (1995) *Am J Pathol*].

Matrix metalloproteinases (MMPs) is a group of zinc-dependent enzymes, play significant roles in such remodeling. Specifically, MMP-2 and MMP-9, known as gelatinase A and B, respectively, are capable of degrading collagen type IV, elastin, and fibronectin and have been identified in the fetal membranes, decidua, and amniotic fluid. Several earlier reports showed that an increase in MMP-9 protein and activity in the fetal membranes, placenta, and amniotic fluid is associated with fetal membrane rupture, term and preterm parturition, and placental detachment from maternal tissue, thus suggesting a role for MMP-9 in these labor-associated events [Hulboy, D. L., Rudolph, L. A., Matrisian, L. M. (1997) *Mol Hum Reprod*, Tsatas, D., Baker, M. S. and Rice, G. E. (1999) *J. Reprod. Fertil*; Maymon, E., Romero, R., Pacora, P., Gervasi, M. T., Gomez, R., Edwin, S. S. and Yoon, B. H. (2000) *Am. J. Obstet. Gynecol*; Yu W H, Woessner Jr J F. (2000) *J Biol Chem*, Xu, P., Alfaidy, N., Challis, J. R. (2002) *J Clin Endocrinol Metab*].

MMPs plays a critical role in the invasive growth of the placenta. MMP-2 localized to the amnion mesenchyme, chorion laeve trophoblast, decidua parietalis, and blood vessels in placenta villi. MMP-9 localized mainly to amnion epithelia, chorion laeve trophoblast, decidua parietalis, and placenta syncytiotrophoblasts. Separate cell culture from different layers of fetal membranes and culture of purified placenta trophoblast cells showed that placenta syncytiotrophoblast and amnion epithelial cells exclusively produced MMP-9; chorion trophoblast cells secreted both MMP-2 and MMP-9 [Xu P., Alefaidy N., Challis J. R. G. (2002) *J Clin Endocrinol Metal*)].

What is needed is a soft natural proteolytic activity of abortive placenta in the present invention to isolate the fetal progenitor cells by minimal manipulation manner.

SUMMARY OF THE INVENTION

Disclosed are novel methods of simultaneous isolation of viable progenitor cells from different organs of an aborted fetus in gestation period of medical pregnancies termination from 18-20 weeks by used a soft natural proteolytic, collagenolytic and fibrinolytic activity of abortive placenta in three open-loops in situ organs perfusion system [Purveyance of tissues of aborted fetuses is performed by Medical Termination of Pregnancy Rules, 2003 (G.S.R. 485(E)—In exercise of powers conferred by section 6 of the Medical Termination of Pregnancy Act, 1971 (34 of 1971), India]. Also studied were collagenolytic, fibrinolytic and proteolytic activity of abortive placenta tissue (18-20 weeks of pregnancy), and total amount viable progenitor cells isolated from different organs of abortive fetus.

The present invention also involved a study of the safety of organ-specific progenitor cells in experimental animals. Results of the experiments showed safety of progenitor cells separated by the methods disclosed herein and absence of toxic and side effects.

BRIEF DESCRIPTION OF THE DRAWINGS

FIG. 1 is a schematic that demonstrates the techniques of three open-loops fetal internal organs perfusion in situ. The fetus was rinsed with the 40% spirit solution, and placed onto a sterile surgical tray. The entire procurement procedure was performed in a sterile environment with a laminar air flow unit providing European Union GMP class A (US class 100) air quality. The abdominal and thoracic cavities accessed through a sternotomy and a midline laparotomy with bilateral subcostal lateral extensions. The umbilical vein, aorta of left heart ventriculus and abdominal part of aorta cannulated with a 16- to 24-gauge cannula according to the size of the vessel, and the cannula ligated with silk. The umbilical vein cannula, aorta of left heart ventriculus and abdominal part of aorta cannulas were then connected to the tissue perfusion tubing, both femoral veins sectioned, and the fetus vessels system perfusion started via three open-loops. Following this step, proteo-, fibrino- and colagenolytic solution (extract of placenta tissue) was perfused in all body of fetus (total time of perfusion—30 min).

FIG. 2 provides a bar graph showing proteolytic, colagenolytic and fibrinolytic activity in tissues of fetal intact internal organs. Maximal levels of azoalbumin (73.77±2.89 µg/1 g tissue per 1 h), azocazein (65.35±2.83 µg/1 g tissue per 1 h) and azocollagen (72.18±2.32 µg/1 g tissue per 1 h) lysis were in tissue of fetal suprarenal glands. High fibrinolytic activity observed in fetal liver (8.49±0.21 µg/1 g tissue per 1 h) and thymus (9.18±0.58 µg/1 g tissue per 1 h).

FIG. 3 provides a bar graph showing comparison of the proteolytic and fibrinolitic activity in tissues of fetal intact internal organs and abortive placentas of the same fetuses. Proteolitic activity of placenta tissue extracts was significantly higher than in tissues of fetal internal organs. Lysis of azoalbumin (782.3±24.69 µg/1 g tissue per 1 h) was 10.6 times higher than in suprarenal glands tissue and 47 times higher than in fetal heart (16.65±0.56 µg/1 g tissue per 1 h). Intensivity of azocazein lysis in placenta (753.7±16.99 µg/1 g tissue per 1 h) was 11.5 times more than in suprarenal glands and 65.9 times higher than in tissue of fetal spleen (11.44±0.93 µg/1 g tissue per 1 h). Collagenolytic activity also have maximal rate in placenta extract (405.3±19.71 µg/1 g tissue per 1 h) and was 5.6 and 49.4 times higher than in suprarenal glands and fetal kidney (8.21±0.26 µg/1 g tissue per 1 h) relatively. In fetal placenta levels of total fibrinolytic activity (760.7±33.65 µg/1 g tissue per 1 h), non-enzymatic (152.7±10.71 µg/1 g tissue per 1 h) and enzymatic fibrinolysis (608.0±24.62 µg/1 g tissue per 1 h) were 11.5, 4.9, 17.2 times more than in suprarenal glands and 98.9, 41.5, 151.6 times higher than in tissue of fetal spleen (7.69±0.27; 3.68±0.27 and 4.01±0.07 µg/1 g tissue per 1 h) correspondingly. After incubation tissue of placenta in presense of PGF2α lysis of azoalbumin (762.0±25.36 µg/1 g tissue per 1 h) and azocazein (745.9±19.80 µg/1 g tissue per 1 h) did not vary, collagenolytic activity increased by 2.1 times (840.6±30.91 µg/1 g tissue per 1 h), total lysis of azofibrin—to 1.4 times (1068.0±36.61 µg/1 g tissue per 1 h), enzymatic fibrinolytic activity—to 1.6 times (985.3±31.96 µg/1 g tissue per 1 h), and non-enzymatic fibrinolysis decreased almost by 2 times (82.71±6.33 µg/1 g tissue per 1 h).

FIG. 4 provides a bar graph showing total amount of progenitor cells, separated from fetal internal organs. In group A (perfusion in situ by non-activated placenta extract) maximum rates of total cells were separated from fetal liver ($40.0\pm5.36\times10^6$ per 1 g tissue), kidney ($34.3\pm4.80\times10^6$ per 1 g tissue), spleen ($32.9\pm5.03\times10^6$ per 1 g tissue) and lung ($15.6\pm2.98\times10^6$ per 1 g tissue). From fetal ileum we separated $36.8\pm3.75\times10^5$ cells per 1 g tissue, suprarenal glands—$40.8\pm5.19\times10^5$ cells per 1 g tissue, heart—$7.2\pm1.60\times10^5$ cells per 1 g tissue, thymus—$98.2\pm9.31\times10^5$ cells per 1 g tissue. In group B (perfusion in situ by PGF2α-activated placenta extract) amount of separated cells increased, but not significant: liver—$44.3\pm6.00\times10^6$ per 1 g tissue, kidney—$38.9\pm5.12\times10^6$ per 1 g tissue, spleen—$38.2\pm5.67\times10^6$ per 1 g tissue, lung—$21.1\pm4.13\times10^6$ per 1 g tissue, ileum $39.7\pm4.32\times10^5$ cells per 1 g tissue, suprarenal glands—$43.4\pm4.95\times10^5$ cells per 1 g tissue, heart—$9.1\pm1.88\times10^5$ cells per 1 g tissue, thymus—$108.4\pm10.26\times10^5$ cells per 1 g tissue.

FIG. 5 provides a bar graph showing percent of viable progenitor cells, separated from internal organs of aborted fetuses. Analyses of viability of separation cells (tripan blue) shows that in group B percent of viable cells was significantly low: liver cells—98.14±0.53% in group A vs 86.15±0.94% in group B; for kidney cells—96.13±0.89% vs 85.02±1.26%; spleen cells—97.41±0.75% vs 91.55±0.92%; lung cells—93.82±1.05% vs 83.76±1.27%; ileum cells—95.60±0.99% vs 88.14±0.86%; suprarenal glands cells—98.15±0.66% vs 89.25±1.37%; heart cells—92.57±1.16% vs 86.15±1.53%; thymus cells—97.63±0.94% vs 90.10±1.19% relatively.

FIG. 6 provides Table 1 representing a design of single-dose toxicity studies. Single-dose Toxicity studies was carried out in 2 rodent species—mice and rats. In this study the same route of administration was used as intended for humans: intravenous fetal progenitor cells injections (rats). In addition, single-dose toxicity in cases of intra peritoneum (in mice) administration was also investigated.

FIG. 7 (Table 2), and FIG. 8 (Table 3) provide the results of single-dose toxicity studies in rats after intravenous fetal progenitor cells injections. Animals were observed for 14 days after the fetal progenitor cells administration, and minimum lethal dose was not established. No mortality and signs of intoxication were observed. In animals observed normal growth of body mass. Pathological changes of organs were not observed.

FIG. 9 (Table 4) provides the results of haematological, coagulation, urinalysis, and blood biochemical studies evidences after intravenous fetal progenitor cells injections: all research parameters did not vary from control levels.

FIG. 10 (Table 5) provides the design of single-dose toxicity studies in mice after intra-peritoneum fetal progenitor cells injections described in the table.

FIG. 11 (Table 6), and FIG. 12 (Table 7) provides the results of single-dose toxicity studies in mice. Animals were observed for 14 days after the intra-peritoneum fetal progenitor cells administration, and minimum lethal dose was not established. No mortality and signs of intoxication were observed. In animals observed normal growth of body mass. Pathological changes of organs were not observed.

FIG. 13 (Table 8) provides the results of haematological, coagulation, urinalysis, and blood biochemical studies evidences that after intra-peritoneum fetal progenitor cells administration all research parameters do not vary from control parameters.

FIG. 14 (Table 9) provides the results of a study demonstrating the influence of human fetal progenitor cells transplantation on the quantity of leukocytes and leukocytes blood formula in Wistar rats. In rats of first and second experimental groups after 4 weeks of subsequent transplantation fetal progenitor cells, quantity of leukocytes in peripheral blood and parameters of leukocytes blood formula were undistinguished from the control.

FIG. 15 (Table 10) provides the results of a study demonstrating the influence of fetal progenitor cells transplantation on the quantity of leukocytes and leukocytes blood formula in Wistar rats. Absolute quantity of eosinophils, basophils, neutrophils (metamyelocytes, band-nucleus and segmented-nucleus neutrophils), lymphocytes (small, moderate and large sizes) and monocytes similarly corresponding to parameters of control animal groups.

FIG. 16 (Table 11) provides the results of a study demonstrating the influence of human fetal progenitor cells transplantation on parameters of myelograms in Wistar rats. In bone marrow of first group's rats, parameters of myeologenesis and lymphopoiesis, index stimulation of neutrophilogenesis, percentage content of erythroblasts, pronormocytes and basophilic normocytes were undistinguished from the controls. At the same time relative quantity of polychromatophilic and oxyphilic normocytes relatively grew to 39.3 and 61.3%. Besides, reduction of coefficient ratio of lymphoid and erythroid germs of the bone marrow to 18.4% were observed. In animals of the second group, such parameters of percentage content in bone marrow as blasts, promyelocytes, myelocytes, metamyelocytes, band-nucleus and segmented-nucleus neutrophils, eosinophils, basophils, monocytes, lymphocytes, plasmatic cells, megakaryocytes, erythroblasts, pronormocytes, basophilic normocytes and similarly index stimulation of neutrophilogenesis corresponded to controls. Quantity of basophilic normocytes decreased to 30.1%. Level of polychromatophilic and oxyphilic normocytes, on the contrary grew up to 1.4 and 2.0 times correspondingly. In animals of the second group, percentage content of pronormocytes in bone marrow was 1.8 times lesser than in rats of the first group. Remaining myelograms parameters in the experimental rat groups were practically similar.

FIG. 17 (Table 12) provides the results of a study demonstrating the influence of human fetal progenitor cells transplantation on erythron of Wistar rats. In animals of the first group observed increase content of hemoglobin in blood to 15.9% and reduction in erythrocyte sedimentation rate to 1.7 times. Quantity of erythrocytes in peripheral blood and color parameter did not vary from the control. In bone marrow was noticed reduction in level of basophilic normocytes to 1.3 times and increase content of polychromatophilic normocytes to 1.2 times. Index stimulation of erythropoiesis rose to 20.4%. In rats of second groups concentration of hemoglobin in blood increased to 21.7%, erythrocytes sedimentation rate reduced to 1.5 times. In bone marrow observed most expressive changes: level of basophilic normocytes decreased to 1.5 times, whereas content of polychromatophilic and oxyphilicnormocytes increased relatively to 1.3 and 1.9 times. Index stimulation of erythropoiesis exceeded control parameters to 38.8%. In peripheral blood various study parameters in rats of first and second group were not apparent, in bone marrow of the second group animals were noticed more higher parameters level of oxyphilic normocytes (to 1.4 times) and index stimulation of erythropoiesis (to 15.3%).

FIG. 18 (Table 13) provides the results of a study demonstrating the dynamics of the contents of mononuclear cells in bone marrow, reticulocytes and human fetal hemoglobin in blood of immunosuppressed rabbits after human fetal progenitor cells transplantation. In busulfan immunosuppressed rabbits on $6^{th}$ day survey quantity of mononuclear cells in bone marrow reduced in comparison to initial data to 30.8%, on $12^{th}$ day—to 23.0%, on $18^{th}$ day—to 31.6%, on $60^{th}$ day—to 16.6%. On $120^{th}$ day experiments quantity of mononuclear cells in bone marrow were undistinguished from the initial data. After introduction of fetal progenitor cells to immunosuppressed rabbits quantity of mononuclear cells in bone marrow similarly reduced: on the $6^{th}$ day—to 29.8%, on $12^{th}$ day—to 17.9%, on $18^{th}$ day—to 22.0%. Restoration of those parameters up to the initial level occurred on $60^{th}$ day—significantly earlier than in animals of control group. On $60^{th}$ and $120^{th}$ day quantity of mononuclear in bone marrow was correspondingly 39.3 and 27.1% higher in rabbits those which were introduced fetal progenitor cells. Reticulocytes contents in bone marrow of control group rabbits on the extent of all experiments remained below the initial level: on $6^{th}$ day—to 2.4 times, on $12^{th}$ day—to 2.3 times, on $18^{th}$ day—to 2.2 times, on $60^{th}$ day—to 1.8 times, on $120^{th}$ day—to 1.3 times. At the same time animals in those introduced fetal progenitor cells, quantity of reticulocytes of bone marrow achieved the initial parameters on $60^{th}$ day of surveillance, but on the $120^{th}$ day content of reticulocytes were 35.2% higher than the initial level. In experimental group rabbits, contents of reticulocytes in bone marrow on $60^{th}$ and $120^{th}$ day of experiments were correspondingly high to 57.4 and 85.0% than in control animals group. In immunosuppressed rabbits blood exhibited trace quantities of fetal hemoglobin (less than 1%), but on $60^{th}$ and $120^{th}$ day level of fetal hemoglobin reduced almost to 2 times. Rabbits, in those intravenously injected with fetal progenitor cells, contents of fetal hemoglobin progressively grew and attained correspondingly to 28.1 and 23.9% on $60^{th}$ and $120^{th}$ day of experiments.

FIG. 19 (Table 14) provides the results of a study demonstrating the dynamics changes of the peripheral blood parameters in immunosuppressed rabbits after transplantation fetal progenitor cells. Contents of blood hemoglobin reduced comparatively to initial level on $12^{th}$ and $18^{th}$ day relatively to 27.0 and 12.9%. On the $60^{th}$ and $120^{th}$ day quantity of hemoglobin did not vary from the initial parameters. Similar dynamics changes surveyed respectively in erythrocytes: its content in blood decreased to 21.3, 32.8 and 15.6% corresponding to $6^{th}$, $12^{th}$ and $18^{th}$ day of experiments and normalized to $60^{th}$ and $120^{th}$ day. Relative quantity of reticulocytes in peripheral blood was sharply reduced on $6^{th}$ and $12^{th}$ day of surveillance. Further, noticed progressive increase level of reticulocytes with normalization of this parameter on $120^{th}$ day. Contents of thrombocytes in blood on $6^{th}$, $12^{th}$ and $18^{th}$ day reduced twice. On $60^{th}$ day noticed increase in its quantity and on $120^{th}$ day level of thrombocytes in blood corresponded to initial parameters. Contents of leukocytes in peripheral blood sharply reduced on $6^{th}$ and $12^{th}$ day and gradually increased from $18^{th}$-$120^{th}$ day of surveillance, but at the end of experiments remained to 13.6% below the initial level. Metamyelocytes on $6^{th}$ and $18^{th}$ day in blood was not determined, but on $60^{th}$ and $120^{th}$ day their percentage of content did not vary from the control. On the background of immunosuppression from $6^{th}$ to $60^{th}$ day was observed degenerative shift of leukocytes formula to the left that evidenced substantial increase relative quantity of band neutrophils. Level of segmented neutrophils also grew up but significantly on the lesser degree. On the $120^{th}$ day surveillance of contents in peripheral blood, band-nucleus and segmented-nucleus neutrophils corresponded to the initial parameters. Relative quantity of basophils reduced only on $120^{th}$ day of surveillance. On the $6^{th}$ and $18^{th}$ day noticed 40% decrease level of eosinophils in blood, but in remaining period of surveillance this parameter did not vary from the initial data. Relative contents of lymphocytes in peripheral blood on $6^{th}$ day reduced to 34.6%, on $12^{th}$ day—to 26.1%, on $18^{th}$ day—to 28.0%, on $60^{th}$ day—to 18.3%. On $120^{th}$ day quantity of leukocytes in blood did not vary from the initial level. Observed substantially decrease in blood monocytes: on $6^{th}$ day—to 2.9 times, on $12^{th}$ day—to 1.7 times, on $18^{th}$ day—to 1.9 times. On the $60^{th}$ day quantity of monocytes in blood were lesser than the initial period only to 22.6%, but on $120^{th}$ day of experiments this parameter already did not vary from the initial level.

FIG. 20 (Table 15) provides the results of a study demonstrating the dynamics changes of absolute parameter content of leukocytes in peripheral blood of immunosuppressed busulfan rabbits after transplantation fetal progenitor cells. Analysis of blood leukogram in absolute numbers evidences that after introduction of busulfan until $60^{th}$ day inclusively, in rabbits observed total leukopenia. However on $120^{th}$ day all the parameters, exclusive of band-nucleus neutrophils and basophils, restored and did not vary from the initial level.

FIG. 21 (Table 16) provides the results of a study demonstrating the influence of human fetal progenitor cells transplantation in relative mass of organs of the reproductive systems. In intact rats after intravenous introduction of fetal progenitor cells relative mass of the investigative reproductive organs were unchanged. Introduction of busulfan to animals caused to twofold decrease in mass of testes and decreased relative mass of epididymises to 25.1%, but does not influence the parameters of ventral and anterior parts of prostate. After transplantation of fetal progenitor cells on the back ground of immunosuppressor busulfan, mass of testes decreased to 28.6%, epididymises—to 19.4%. Repeated introduction of fetal progenitor cells in immunosuppressed rats normalized mass parameters of testes and epididymises.

FIG. 22 (Table 17) provides the results of a study demonstrating the influence of fetal progenitor cells transplantation on the content of testosterone and biological active luteinizing hormone in blood plasma of the rats Wistar. Concentration parameters of testosterone in blood plasma and contents of biological active luteinizing hormone in blood after transplantation of fetal progenitor cells in intact rats were unchanged. Busulfan reduced level of testosterone to 4.1 times and caused to twofold decrease in content of biological active luteinizing hormone in blood. In animals in which busulfan and fetal progenitor cells were introduced, and similarly in immunosuppressed rats where repeated transplantation of fetal progenitor cells were provided, the content of testosterone in blood plasma and content of biological active luteinizing hormone in blood did not vary from the control.

FIG. 23 (Table 18) provides the results of a study demonstrating the influence of fetal progenitor cells transplantation on the activity of 3β-hydroxyl-$\Delta^5$-steroid-dehydrogenase in testes of rats Wistar. Activity of 3β-hydroxyl-$\Delta^5$-steroid-dehydrogenase after transplantation of fetal progenitor cells in intact rats tallied with the control parameters. Introduction of busulfan caused decrease in activity of 3β-hydroxyl-$\Delta^5$-steroid-dehydrogenase to 26.8 and 28.2% correspondingly in recalculation on 1 mg of protein and 1 g of testes tissue. After introduction of busulfan and transplantation of fetal progenitor cells activity of 3β-hydroxyl-$\Delta^5$-steroid-dehydrogenase did not vary from the control. Repeated introduction of fetal progenitor cells to immunosuppressed animals increased the activity of 3β-hydroxyl-$\Delta^5$-steroid-dehydrogenase to 1.3 times.

FIG. 24 (Table 19) provides the results of a study demonstrating the influence of fetal progenitor cells transplantation on concentration of spermatozoids in epididymises of the Wistar rats. Concentration of spermatozoids in epididymises of intact rats those were injected fetal progenitor cells matched with control. Busulfan reduced the level of spermatozoids to 2.1 times. After introduction of busulfan and transplantation of fetal progenitor cells concentration of spermatozoids did not vary form the control parameters. Repeated intravenous introduction of fetal progenitor cells in immunosuppressed animals roused increase contents of spermatozoids in epididymises to 44.8% in comparison with control group.

FIG. 25 (Table 20) provides the results of a study demonstrating the influence of fetal progenitor cells transplantation on index of spermatogenesis in testes of the rats Wistar. Introduction of fetal progenitor cells in intact rats increased the index of spermatogenesis to 35.0%, whereas busulfan decreased those parameters to 2.3 times. In introduction of busulfan and transplantation of fetal progenitor cells observed increase in index of spermatogenesis comparative to control on 29.9%, and after repeated intravenous introduction of fetal progenitor cells in immunosuppressed animals index of spermatogenesis increased on 71.7%.

FIG. 26 (Table 21) provides the results of a study demonstrating the influence of fetal progenitor cells transplantation on content of fructose in anterior part of prostates in the rats Wistar. Content of the fructose in anterior part of prostates in transplantation fetal progenitor cells in intact animals grew to 34.0%. Busulfan decreased level of fructose to 25.5%. After introduction of busulfan and fetal progenitor cells content of fructose in the anterior part of prostrate coordinated with the control, but subsequent repeated transplantation of fetal progenitor cells in immunosuppressed rats were 88.3% higher, than in animal of the control group.

FIG. 27 provides photographs of human abortive placenta after an 18-week gestation term.

DETAILED DESCRIPTION OF THE INVENTION

Disclosed herein are novel method for procuring progenitor cells: the method involve the use of fetal progenitor cells isolated from the organs of aborted fetuses after medical termination of pregnancy; the fetal progenitor cells are available for therapeutic use in accordance with organ-specific cell therapy and uses known to those skilled in the art. The disclosed invention comprises the isolation of said progenitor cells comprising the use of natural collagenolytic, fibrinolytic and proteolytic activity; in certain embodiments, the collagenolytic, fibrinolytic and proteolytic extract are derived from the tissue of the abortive placenta.

Biological safety of fetal progenitor cells is provided by stringent control of bacteria, fungus and virus contamination in all stages of production—from procurement of anatomical material of aborted fetus which was destroyed as the result of medical termination of pregnancy till the preparation of cells suspension for study or treatment.

In accordance with the method disclosed herein, collection of fetal anatomical material is stringently controlled through numerous protocols. Purveyance of tissue of aborted fetuses was performed by Medical Termination of Pregnancy Rules, 2003. (G.S.R. 485(E)—In exercise of powers conferred by section 6 of the Medical Termination of Pregnancy Act, 1971 (34 of 1971), India). As a first step, adherence to Fetal Material Dispatch (Requirements to Donors) is mandated. The inclusion criteria for selection of donors requires the following: the donor should be 18 years of age or above; the donor should be free from all the infectious diseases viz: HIV-1 & 2, HBV, HCV, CMV, VDRL; the duration of pregnancy should be between 18 to 20 weeks; the donor should undergo medical termination of pregnancy (MTP) and give her consent for the same independently of personnel who carries out the cell isolation. Exclusion criteria for donor: age of the pregnant women is less than 18 years; absence of "The Informed Consent for HIV Test", "The Informed Consent for MTP" or "The Informed Consent for the collection of the abortive material" of the pregnant women; period of pregnancy is above 20 weeks; pregnant women is detected with infectious diseases including HIV 1/2, HCV, HBV, CMV, VDRL; known history for intrauterine fetal death; if the aborted material is collected as a result of spontaneous abortion; known for clear signs of congenital anomalies or infection in fetus. As a second step, a screening test for the donors is conducted. All the screening tests for the selection of donor were performed as per the "Guidelines for Stem Cell Research and Therapy (2007)" and "Guidelines for Stem Cell Research (2013)" jointly issued by Department of Biotechnology & Indian Council of Medical Research (Ministry of Health and Family Welfare, India). The donors are tested for the infectious diseases including, but not limited to, HIV 1/2, HCV, HBV, CMV, and VDRL. As contemplated herein the medical termination of pregnancy (MTP) is performed by a recognized gynecologist at the gynecology department of a hospital. In order to fill "The Informed Consent form for MTP" all the selection criteria must be fulfilled. A separate consent form for MTP may also be provided by hospital where the MTP is to take place. The "Informed consent form for donating the aborted fetal and placenta/cord tissue for research" is provided by the hospital, where the pre-abortion tests and MTP is carried out. Procuring anatomical material is implemented only by obstetrician-gynaecologist and nurses of the medical institutions in which MTP is performed.

The collection of fetal tissue material from aborted foetuses was performed in sterile condition, in accordance with the medical and health regulations mandated by the Indian government. Transportation of the fetal anatomical material (fetus and placenta) is performed in special cryo-bags, which eliminates the possibilities of microbial contamination while transportation. Preliminary processing includes washing of anatomical material from blood and washed out solution taken for emergency microbial contamination analysis by the method of express endotoxin analysis.

Fetal placenta extract processing. Large vessels were removed using blunt dissection and leaving only chorionic villous tissue, which was further dissected into 20 mg pieces. Tissues were extensively washed in sterile phosphate-buffered saline (PBS), and half of tissues were 5 min incubated in the presence of 25 µg/mL PGF2α (Enzaprost F, Chinoin Pharmaceutical and Chemical Works Private Co. Ltd., Hungary) for activation of proteolytic activity. Second half of tissue was not incubated, and used for study of natural proteolytic activity of placenta. Then all placenta villous tissues were homogenaized in tissue homogenaizer (Wheaton, USA). After centrifugation total volume of 25% supernatant was from 50 to 100 ml. Collagenase in human tissue is generally present in an inactivated form and thus needs to be activated. A 100-mL of supernatant was mixed with 80 mL of 125 mM borate buffer (pH 7.5) containing 10 mM $CaCl_2$. Then, 10 mL of 43 µM trypsin was added and the solution was incubated at 37° C. for 10 min. After collagenase activation, 10 mL of 3.0 mg/mL soybean trypsin inhibitor was added.

The process of fetal progenitor cells isolation involves a three open-loops internal organs perfusion in situ (FIG. 1). Blood from fetal vascular system was removed by perfusion of 1000 ml ice-cold D-PBS without calcium and magnesium. Remaining red blood cells in fetus vascular system were lysed by perfusion of ice-cold solution containing $NH_4Cl$, $KHCO_3$, and EDTA. The fetal vascular system was then perfused by ice-cold D-PBS without calcium and magnesium. After this fetal vascular system was perfused by 25% fetal placenta tissue extract (placenta from same fetus) with $CaCl_2$. Then fetal vascular system was perfused by D-PBS solution containing EDTA. Finally, fetus vascular system was perfused by ice-cold D-PBS without calcium and magnesium.

Soft and disintegrate encapsulated parenchymal organs (except lungs) were transferred into a 100-mm Petri dishes. The capsules were ruptured with forces and the mechanical disruption of the parenchymal organs was completed by scraping tissues with a sterile, disposable cell scrapers. This primary cells material was filtered through a sterile 500-µm nylon mesh. The cells pellet was washed 2-4 times and transferred into cryo-vials after adding cryoprotector (DMSO, 5% final concentration). Then cells suspensions were cryopreserved.

Non-parenchymal organs and lungs were transferred into 100-mm Petri dishes. Organs were dissected into small fragments and transferred into tissue homogenizer, and minced into indiscrete mass. Cells were washed out from homogenizer walls and piston with Hanks' solution into graduated test tubes passing them through blood transfusion filter and then through needles of more and more narrower diameter. After centrifugation the cells pellet was washed 2-4 times and transferred into cryo-vials after adding cryoprotector (DMSO, 5% final concentration). Then cells suspensions were cryopreserved.

Biosafety control. A portion of harvested cells were directed to biosafety lab and microbiological lab (the ready cells suspensions were studied for bacterial sterility, contamination of viruses, fungus and transmission infections: HIV1/HIV2, HbsAg, HCV, HBV, HSV 1/2, CMV, *Treponema pallidum, Toxoplasma gondii*, Micoplasma, Ureaplasma, Chlamidii, EBV by means of polymerase chain reaction). Cell viability was determined with Trypan Blue.

Passportization (analytical characterisation) of fetal progenitor cells suspensions. Progenitor cells passport (certificate of quantity and quality) contain: result of screening test for donors of anatomical material (ELISA): HIV 1, HIV 2, HBV, HCV, CMV, HTLV, VDRL; Cell Test-Control (PCR): HIV 1, HIV 2, HBV, HCV, CMV, HTLV, HSV1 &2, EBV, *Treponema pallidum, Mycoplasma hominis, Ureaplasma* sp., *Chlamydia* all species, *Toxoplasma gondii*; Microbiologist Control Sterility Testing: Aerobic m/o, Anaerobic m/o, Fungus; Gestation Period of the Human Fetus: 18-20 weeks; Progenitor cells types: liver, brain, spinal cord, gastric, intestinal, lung, kidney, skin, bone, oculus, heart, thymus, spleen, pancreas, muscle, vessels; Progenitor cells suspension quantity & quality: total cells amount per 1 ml, live-cells amount per 1 ml, amount of CFU per 1 ml, karyotyping (FISH), transplantation unit (amount of CFU/amount of living cells; Cryo-Protector: DMSO, PVG, any other; CD Markers: if it's necessary; HLA Typing: if it's necessary. Following the above steps, progenitor cells suspensions are ready for use: liver progenitor cells, intestinal progenitor cells, lung progenitor cells, kidney progenitor cells, heart progenitor cells, suprarenal glands progenitor cells, thymus progenitor cells, and spleen progenitor cells.

To verify the proteolytic activity of the abortive placenta tissue extract were investigated proteolytic and colagenolitic activity of fetal organs tissue and fetal placenta extract. Proteolytic and colagenolitic activities were studied by method of intensivity azoalbumin, azocazein and azocollagene lysis estimation. Tissue fibrinolytic activity was investigated by azofibrin lysis. For analysis of non-enzymatic fibrinolysis epsilon-aminocaproic acid was used. As shown in FIG. 2, maximum levels of azoalbumin, azocazein and azocollagen lysis were in tissue of fetal suprarenal glands. High fibrinolytic activity was observed in fetal liver. Proteolitic activity of placenta tissue extract was signiflcally higher than in tissues of fetal internal organs (FIG. 3). Lysis of azoalbumin was 11 times higher than in suprarenal glands tissue and 47 times higher than in fetal heart. Intensivity of azocazein lysis in placenta was 12 times more than in suprarenal glands and 66 times higher than in tissue of fetal spleen. Collagenolytic activity also have maximum rate in placenta extract and was 6 and 49 times higher than in suprarenal glands and fetal kidney relatively. In fetal placenta levels of total fibrinolytic activity, non-enzymatic and enzymatic fibrinolysis were 12, 5, 17 times more than in suprarenal glands and 99, 42, 152 times higher than in tissue of fetal spleen correspondingly. After incubation tissue of placenta in presence of PGF2α lysis of azoalbumin and azocazein did not vary, collagenolytic activity increased by 2 times, total lisys of azofibrin—to 1.4 times, enzymatic fibrinolytic activity—to 1.6 times, and non-enzymatic fibrinolysis decreased almost by 2 times. The results of these studies indicate that (1) the proteolytic, collagenolytic and fibrinolytic activity of placenta extract are significantly higher than in the fetal organs tissues, and (2) in placenta chorion tissue preliminary proteolysis activation by prostaglandin F2α does not significantly further enhance placental tissue proteolysis. Thus, the natural proteolytic activity of the placenta is enough for the soft destruction of the immature extracellular matrix of the fetus organs in order to isolate progenitor cells.

Total amount of progenitor cells, separated from fetal internal organs (FIG. 4), in group A (perfusion in situ by natural proteolytic activity of the placenta extract) was maximum in liver, kidney, spleen and lung. From fetal ileum we separated 2.9-4.2 millions cells per 1 g tissue, suprarenal glands—3.0-5.0, heart—0.4-1.2, thymus—8.1-12.2 millions cells per 1 g tissue. In group B (perfusion in situ by PGF2α-activated placenta extract) amount of separated cells increased, but not significantly. Analyses of viability of separated cells show (FIG. 5) that in group B percent of viable cells was significantly low. Thus, fetal placenta extract activation by PGF2α increases the amount of separated cells but decrease number of viable cells.

Single-dose toxicity studies carried out in rats (FIG. 6) shows that after the fetal progenitor cells administration minimum lethal dose were not established. No mortality and signs of intoxication were observed. Normal growth of body mass was observed in animals (FIG. 7). Pathological changes of organs were not observed (FIG. 8). Results of haematological, coagulation, urinalysis, and blood biochemical studies evidences after intravenous fetal progenitor cells injections: all research parameters did not vary from control levels (FIG. 9).

Single-dose toxicity studies carried out in mice (FIG. 10) show that after the fetal progenitor cells administration minimum lethal dose was not established. No mortality and signs of intoxication were observed. Normal growth of body mass was observed in animals (FIG. 11). Pathological changes of organs were not observed (FIG. 12). Results of haematological, coagulation, urinalysis, and blood biochemical studies evidences after intravenous fetal progenitor cells injections: all research parameters did not vary from control levels (FIG. 13).

For investigation of possible toxic effects of the fetal progenitor cells on blood system, were conducted experiments on rats (Wistar) and rabbits (Grey giant). All animals were introduced fetal progenitor cells once intravenously, using cells isolated from the fetal internal organs. Rats Wistar: First group (group 1)—14 rats (7 males, 7 females). Characteristics of fetal progenitor cells: Gestation term—18-20 weeks; total quantity of cells—$31.05\times10^6$/rat; quantity of spleen progenitor cells—$8.00\times10^6$/rat; quantity of heart progenitor cells—$2.50\times10^5$/rat; quantity of lung progenitor cells—$4.00\times10^6$/rat; quantity of kidney progenitor cells—$8.00\times10^6$/rat; quantity of suprarenal glands progenitor cells—$2.50\times10^5$/rat; quantity of ileum progenitor cells—$3.00\times10^5$/rat; quantity of thymus progenitor cells—$2.50\times10^5$/rat; quantity of liver progenitor cells—$10.00\times10^6$/rat. Second group (group 2)—14 rats (7 males, 7 females). Characteristics of fetal progenitor cells: Gestation term—18-20 weeks; total quantity of cells—$46.575\times10^6$/rat; quantity of spleen progenitor cells—$12.00\times10^6$/rat; quantity of heart progenitor cells—$3.75\times10^5$/rat; quantity of lung progenitor cells—$6.00\times10^6$/rat; quantity of kidney progenitor cells—$12.00\times10^6$/rat; quantity of suprarenal glands progenitor cells—$3.75\times10^5$/rat; quantity of ileum progenitor cells—$4.50\times10^5$/rat; quantity of thymus progenitor cells—$3.75\times10^5$/rat; quantity of liver progenitor cells—$15.00\times10^6$/rat. Control group (intravenous 0.9% sodium chloride injection)—14 animals (7 males, 7 females). All investigation (analysis of peripheral blood and myelograms) were conducted after 28 days of subsequent transplantation fetal progenitor cells.

In rats of first and second experimental groups after 4 weeks of subsequent transplantation fetal progenitor cells, quantity of leukocytes in peripheral blood and parameters of leukocytes blood formula were undistinguished from the control (FIG. 14). Absolute quantity of eosinophils, basophils, neutrophils (metamyelocytes, band-nucleus and segmented-nucleus neutrophils), lymphocytes (small, moderate and large sizes) and monocytes similarly corresponding to parameters of control animal groups (FIG. 15). In bone marrow of first group's rats, parameters of myeologenesis and lymphopoiesis, index stimulation of neutrophilogenesis, percentage content of erythroblasts, pronormocytes and basophilic normocytes were undistinguished from the controls (FIG. 16). At the same time relative quantity of polychromatophilic and oxyphilic normocytes grew up correspondingly to 39% and 61%. Besides, reduction coefficient ratio of lymphoid and erythroid germs of the bone marrow to 18% were observed. In animals of the second group, such parameters of percentage content in bone marrow as blasts, promyelocytes, myelocytes, metamyelocytes, band-nucleus and segmented-nucleus neutrophils, eosinophils, basophils, monocytes, lymphocytes, plasmatic cells, megakaryocytes, erythroblasts, pronormocytes, basophilic normocytes and similarly index stimulation of neutrophilogenesis corresponded to controls. Quantity of basophilic normocytes decreased to 30%. Level of polychromatophilic and oxyphilic normocytes, on the contrary grew to 1.4 and 2.0 times correspondingly. In animals of the second group, percentage content of pronormocytes in bone marrow was 1.8 times lesser than in rats of the first group. Remaining myelograms parameters in the experimental rat groups were practically similar.

In animals of the first group increase in the content of hemoglobin in blood to 15.9% and reduction in erythrocyte sedimentation rate to 1.7 times (FIG. 17) was observed. Quantity of erythrocytes in peripheral blood and color parameters did not vary from the control. In bone marrow reduction in level of basophilic normocytes to 1.3 times and increase content of polychromatophilic normocytes to 1.2 times were noticed. Index stimulation of erythropoiesis rose to 20%. In rats of second groups concentration of hemoglobin in blood increased to 22%, erythrocytes sedimentation rate reduced to 1.5 times. In bone marrow the most expressive changes were observed: level of basophilic normocytes decreased by 1.5 times, whereas content of polychromatophilic and oxyphilicnormocytes increased correspondingly to 1.3 and 1.9 times. Index stimulation of erythropoiesis exceeded control parameters to 39%. In peripheral blood, various study parameters in rats of first and second group were not apparent, in bone marrow of the second group animals were noticed more higher parameters level of oxyphilic normocytes (to 1.4 times) and index stimulation of erythropoiesis (to 15%).

Blood system toxicity in rabbits Grey Giant. Experiments were conducted in immunosuppressed rabbits: before transplantation of fetal progenitor cells (experiment) or intravenous introduction of 0.9% sodium chloride solution (control) all rabbits per os received busulfan at the doze of 2 mg/kg body mass once a day in course of 5 days. Total doze of busulfan consisted of 10 mg/kg body mass. Mortality of animals due to busulfan consisted of 35%. In experiments survived rabbits were used. Experimental group—15 animals (8 males, 7 females). Characteristics of fetal progenitor cells: Gestation term—18-20 weeks; total quantity of cells—$134.20 \times 10^6$/rabbit; quantity of spleen progenitor cells—$32.00 \times 10^6$/rabbit; quantity of lung progenitor cells—$16.00 \times 10^6$/rabbit; quantity of heart progenitor cells—$10.00 \times 10^5$/rabbit; quantity of kidney progenitor cells—$32.00 \times 10^6$/rabbit; quantity of suprarenal glands progenitor cells—$10.00 \times 10^5$/rabbit; quantity of ileum progenitor cells—$12.00 \times 10^5$/rabbit; quantity of thymus progenitor cells—$10.00 \times 10^5$/rabbit; quantity of liver progenitor cells—$40.00 \times 10^6$/rabbit. Control group—15 animals (8 males, 7 females): busulfan immunosuppressed rabbits, those were injected 0.9% sodium chloride solution instead of fetal progenitor cells. In rabbits 1.5 ml of blood were collected from right or left vena auricularis with the help of heparinized syringe. Bone marrow collected from femur by the washing method under the ether anesthesia. Analyzed hematological parameters of peripheral blood, cells constitution of bone marrow and contents of human fetal hemoglobin in blood on 0-day (initial data), $6^{th}$ (after 24 hours of subsequent last introduction of busulfan), $12^{th}$, $18^{th}$, $60^{th}$ and $120^{th}$ day following transplantation of fetal progenitor cells (experimental group) or intravenous introduction of 0.9% sodium chloride solution (control group).

In busulfan immunosuppressed rabbits on $6^{th}$ day survey quantity of mononuclear cells in bone marrow reduced in comparison to initial data to 31%, on $12^{th}$ day—to 23%, on $18^{th}$ day—to 32%, on $60^{th}$ day—to 17%. On $120^{th}$ day experiments quantity of mononuclear cells in bone marrow were undistinguished from the initial data. After introduction of fetal progenitor cells to immunosuppressed rabbits quantity of mononuclear cells in bone marrow similarly reduced: on the $6^{th}$ day—to 30%, on $12^{th}$ day—to 18%, on $18^{th}$ day—to 22%. Restoration of those parameters up to the initial level occurred on $60^{th}$ day—significantly earlier than in animals of control group. On $60^{th}$ and $120^{th}$ day quantity of mononuclear in bone marrow was correspondingly 39 and 27% higher in rabbits those which were introduced fetal progenitor cells. Reticulocytes contents in bone marrow of control group rabbits on the extent of all experiments remained below the initial level: on $6^{th}$ day—to 2.4 times, on $12^{th}$ day—to 2.3 times, on $18^{th}$ day—to 2.2 times, on $60^{th}$ day—to 1.8 times, on $120^{th}$ day—to 1.3 times. At the same time animals in those introduced fetal progenitor cells, quantity of reticulocytes of bone marrow achieved the initial parameters on $60^{th}$ day of surveillance, but on the $120^{th}$ day content of reticulocytes were 35% higher than the initial level. In experimental group rabbits, contents of reticulocytes in bone marrow on $60^{th}$ and $120^{th}$ day of experiments were correspondingly high to 57% and 85% than in control animals group. In immunosuppressed rabbits blood exhibited trace quantities of fetal hemoglobin (less than 1%), but on $60^{th}$ and $120^{th}$ day level of fetal hemoglobin reduced almost to 2 times. Rabbits, in those intravenously injected with fetal progenitor cells, contents of fetal hemoglobin progressively grew and on $60^{th}$ and $120^{th}$ day experiments correspondingly attained to 28 and 24% (FIG. 18). Contents of blood hemoglobin reduced comparative to initial level on $12^{th}$ and $18^{th}$ day correspondingly to 27% and 13%. On the $60^{th}$ and $120^{th}$ day quantity of hemoglobin did not vary from the initial parameters. Similar dynamics changes surveyed respectively in erythrocytes: its content in blood decreased to 21, 33 and 15.6% corresponding to $6^{th}$, $12^{th}$ and $18^{th}$ day of experiments and normalized to $60^{th}$ and $120^{th}$ day. Relative quantity of reticulocytes in peripheral blood was sharply reduced on $6^{th}$ and $12^{th}$ day of surveillance. Further, noticed progressive increase level of reticulocytes with normalization of this parameter on $120^{th}$ day. Contents of thrombocytes in blood on $6^{th}$, $12^{th}$ and $18^{th}$ day reduced twice. On $60^{th}$ day noticed increase in its quantity and on $120^{th}$ day level of thrombocytes in blood corresponded to initial parameters. Contents of leukocytes in peripheral blood sharply reduced on $6^{th}$ and $12^{th}$ day, gradually increased from $18^{th}$-$120^{th}$ day of surveillance, but at the end of experiments remained to 14% below the initial level. Metamyelocytes on $6^{th}$ and $18^{th}$ day in blood was not determined, but on $60^{th}$ and $120^{th}$ day their percentage of content did not vary from the control. On the background of immunosuppression from $6^{th}$ to $60^{th}$ day observed degenerative shift of leukocytes formula to the left that evidenced substantial increase relative quantity of band neutrophils. Level of segmented neutrophils also grew but significantly on the lesser degree. On the $120^{th}$ day surveillance of contents in peripheral blood, band-nucleus and segmented-nucleus neutrophils corresponded to the initial parameters. Relative quantity of basophils reduced only on $120^{th}$ day of surveillance. On the $6^{th}$ and $18^{th}$ day noticed 40% decrease level of eosinophils in blood, but in remaining period of surveillance this parameter did not vary from the initial data. Relative contents of lymphocytes in peripheral blood on $6^{th}$ day reduced to 35%, on $12^{th}$ day—to 26%, on $18^{th}$ day—to 28%, on $60^{th}$ day—to 18%. On $120^{th}$ day quantity of leukocytes in blood did not vary from the initial level. Observed substantial decrease in blood monocytes: on $6^{th}$ day—to 2.9 times, on $12^{th}$ day—to 1.7 times, on $18^{th}$ day—to 1.9 times. On the $60^{th}$ day quantity of monocytes in blood were lesser than the initial period only to 23%, but on $120^{th}$ day of experiments this parameter already did not vary from the initial level (FIG. 19). Analysis of blood leukogram in absolute numbers evidences that after introduction of busulfan until $60^{th}$ day inclusively, in rabbits total leukopenia was observed. However on $120^{th}$ day all the parameters, exclusive of band-nucleus neutrophils and basophils, restored and did not vary from the initial level (FIG. 20).

Carcinogenicity: Carcinogenicity of fetal progenitor cells was studied by intravenous and ectopic introduction of cells to immunocompromized (busulphan, 1 mg per 1 kg body mass, once in a day, course of 7 days) rats, rabbits, guinea pigs and mice. The cells were provided to the animals as follow: intradermally, subcutaneously, intramuscularly, in anterior chamber of eye, under the capsule of kidneys, in omentum, in liver tissue, in spleen tissue, in lung tissue, in the wall of small intestine, in wall of large intestine, in the wall of the stomach, in sternum. After 6, 12 and 18 months after ectopic introduction of fetal progenitor cells in the research organs macroscopic and microscopic signs of tissue malignancy were not observed.

Reproductive toxicity: Experiments for assessing reproductive toxicity were conducted in mature male rats Wistar. The control group consisted of 8 intact males, and four experimental groups were formulated: Group 1: Transplantation of fetal progenitor cells in intact rats (n=5). The investigation was conducted after 30 days of subsequent introduction of fetal progenitor cells. Group 2: Introduction of busulfan in intact rats (n=10). Group 3: Introduction of busulfan and transplantation of fetal progenitor cells (n=16). Experiments conducted after 30 days of subsequent introduction of fetal progenitor cells. Group 4: Repeated introduction of fetal progenitor cells in immunosuppressed rats (n=16). Experiments conducted after 30 days following repeated introduction of fetal progenitor cells. The characteristics of fetal progenitor cells comprised the following: Gestation term—18-20 weeks; total quantity of cells—$62.10 \times 10^6$/rat; quantity of spleen progenitor cells—$16.00 \times 10^6$/rat; quantity of heart progenitor cells—$5.00 \times 10^5$/rat; quantity of lung progenitor cells—$8.00 \times 10^6$/rat; quantity of kidney progenitor cells—$16.00 \times 10^6$/rat; quantity of suprarenal glands progenitor cells—$5.00 \times 10^5$/rat; quantity of ileum progenitor cells—$6.00 \times 10^5$/rat; quantity of thymus progenitor cells—$5.00 \times 10^3$/rat; quantity of liver progenitor cells—$20.00 \times 10^6$/rat. Fetal progenitor cells were injected via syringe in jugular vein after venal section under anesthesia (nembutal, 40 mg per 1 kg body mass, intra-peritoneal). Busulfan injected intra-peritoneal, dose of 1 mg per kg body mass, once in a day during the course of 7 days; the total dose of busulfan consisted of 7 mg per kg body mass. The mortality after injecting busulfan consisted of 53%. For purposes of the experiments, surviving animal were taken. Ventral and anterior parts of prostate glands, testes and epididymises were isolated after mortification of animals under ether anesthesia. The isolated organs were weighed in electronic weighing balance (Sartorius). The pieces of ventral part prostate glands and testes tissues were fixed in the Buena liquid [Volkova O. V., Eletckiy Yu. K. (1982) Moscow: Medicine], and poured into paraffin. The spermatogenesis index was determined in the sections of testes [Ukhov Yu. I., Astrakhancev A. F. (1983) *Ach Anat Histol Embryol*]. In epididymises amount of spermatozoids were counted. Isolated epididymises placed in 2 ml of 0.9% sodium chloride solution, were dissected transversely and washed spermatozoids in course of 2 min by actively stirring. Calculation of spermatozoids in the suspension was performed using a haemocytometer [Sanotckiy I. V., Fomenko V. N., Salnikova M. C. et al. (1978) *Method Recom* Moscow: Ministry of Health USSR]. Contents of fructose in homogenate of anterior part of the prostate were determined in spectrophotometric (wave length of 415 nm) by oxymethylfurfurol—product reaction of hexose with resorcinol in acidic medium [Kochetov G. A. (1980)—Moscow: High School]. Contents of testosterone in blood plasma were determined radio-immunological method using set of reagents "RIA-TESTOSTERONE-PR" manufacturer IBOCH NAS, Belarus. Radioactivity assay measured with the help of γ-Spectrometer Company Beckman (USA) using program of Beckman ImmunoFit EIA/RIA Analysis, Version 1.00. Contents of biological active luteinizing hormone were determined by the method Van Damme [Van Damme M. P., Robertson D. M., Diczfalusy E. (1974) *Acta Endocrinol*] in modification of Baraghini [Baraghini G. F., Celani M. F., Zaidi A. K. et al. (1984) *J Endocrinol Invest*], the principle of which concludes in measuring content of testosterone formed in incubation of Leidigs' cells suspensions isolated from rats testes age of 8 weeks, with the samples of plasma, diluted in the ratio of 1:10. For plotting calibration curve, human luteinizing hormone (LH) was used, standardized by the first International standards of drug substance LH 68/40 (Sigma, USA). Activity of $3\beta$-hydroxyl-$\Delta^5$-steroid-dehydrogenase in 5% tissue homogenate of the testes was determined by spectrophotometric method [Reznikov A. G., Demchenko V. M., Neshimenko O. V. (1976) *Physiological J AS USSR*] using dehydro-epiandrosterone in the rate of precursors of the testosterone biosynthesis. Activities of $3\beta$-hydroxyl-$\Delta^5$-steroid-dehydrogenase were recalculated on organ in the whole, 1 g of tissue and on 1 mg of protein. Contents of the protein in tissue homogenate of testes were determined by the method Lowry [Lowry J. H., Rosebrough N. J., Farr A. L., Randall R. J. (1951) *J Biol Chem*]. Statistical workout of the data performed using Students' t-criteria.

It was determined that transplantation of human fetal progenitor cells in intact rats did not exhibit toxic effect on spermatogenic epithelium of testes (FIG. 21). On the contrary after introduction of human fetal progenitor cells, stimulation of spermatogenesis (that evidences increase parameter of spermatogenesis index and fructose content in the anterior part of the prostates) were observed (FIG. 22-26). Busulfan shows expressed toxic effect in the reproductive system of the Wistar line male rats: Under the influence of this immunosuppressor mass of testes decreased to 2.0 times, concentration of testosterone in blood plasma decreased to 4.1 times, content of biological active luteinizing hormone in blood decreased to 2.0 times, activity of $3\beta$-hydroxyl-$\Delta^5$-steroid-dehydrogenase reduces to 27%, concentration of spermatozoids in epididymises decreased to 2.1 times, index of spermatogenesis decreased to 2.3 times, content of fructose in the anterior part of prostates decreased to 26%. Transplantation of fetal progenitor cells, performed on the back ground of injecting busulfan to animals, correspondingly deteriorates toxic effect of this immunosuppressor in the reproductive system of male rats, and repeated transplantation of human fetal progenitor cells completely restores hormonal regulation of spermatogenesis, and similarly the functional condition of spermatogenic epithelium of the testes.

Discussion

The results of experiments indicate that the proteolytic, fibrinolytic and collagenolytic activities in chorionic tissue of the abortive placenta in gestation terms 18-20 weeks are significantly higher than in the internal organs of the fetus of the same gestational age. ECM remodeling in the fetal organs is necessary for tissue growth and morphogenesis, and matrix metalloproteinases (MMPs) are the main mediators of ECM degradation. They are thought to play important roles during embryonic development, as ECM remodeling is a critical component of tissue growth and morphogenesis. The activity of MMPs during embryonic development may extend to more than the removal of unwanted ECM molecules. It is now clear that MMPs not only remodels the ECM, but also influence many cellular functions. MMP activity may be required during development and normal physiology in several ways: (1) to degrade ECM molecules and allow cell migration; (2) to alter the ECM microenvironment and result in alteration in cellular behavior; (3) to modulate the activity of biologically active molecules by direct cleavage, release from bound stores, or the modulating of the activity of their inhibitors [Vul T. H, Werb Z. (2000) Matrix metalloproteinases: effectors of development and normal physiology Gen Develop 14: 2123-2133].

In placenta proteolysis is associated mainly with the invasive growth that proposes more intensive degradation of mature extracellular matrix components of the uterus endometrium. MMPs expressed at high mRNA levels in the first-trimester trophoblast of the human placenta [Hiden U. et al. (2008) *Diabetes*]. The prominent expression of MT1-MMP early in gestation suggests a major role in processes involved in early placental development. This notion is further supported by its predominant presence in the HLA-G-expressing trophoblast subpopulation, which represents the invasive extravillous trophoblast. The high MT1-MMP expression in the HLA-G-positive trophoblasts is in accordance with results of in situ hybridization in first-trimester placental tissue [Bjorn S F, Hastrup N, Lund L R, Dano K, Larsen J F, Pyke C: (1997) *Mol Hum Reprod*]. This is consistent with our findings that proteolytic activities of placenta tissue extract was significantly higher than in tissues of fetal internal organs. In fact, the higher level of proteolysis in placenta extracts can breakdown extracellular matrix (ECM) in the internal organs of the fetus, where ECM is immature and easily lends itself to proteolytic degradation. Immunolocalization studies revealed a specific distribution pattern for MMP-2 and MMP-9 show, that MMP-2 was localized to the amnion mesenchyme, chorion laeve trophoblast, decidua parietalis, and blood vessels in placenta villi. MMP-9 was localized mainly to amnion epithelia, chorion laeve trophoblast, decidua parietalis, and placenta syncytiotrophoblasts. Separate cell culture of purified placenta trophoblast cells showed that placenta syncytiotrophoblast and amnion epithelial cells exclusively produced MMP-9; chorion trophoblast cells secreted both MMP-2 and MMP-9. An increase in MMP-9 expression may contribute to degradation of the ECM in the placenta. In addition, MMPs to involve in multiple steps of trophoblast invasion: penetration of the endometrial epithelium, rupture of the endometrial basement membrane, infiltration through the endo- and myometrium, penetration and conversion of the maternal spiral arteries, and finally, cessation of invasion [Xu P., Alfaidy N., Challis J. R. G. (2002) *J Clin Endocrinol Metab*]. Xu P. et al. studies have compared cytotrophoblast from the first and third trimesters: for example, in human preimplantation embryos, MMP-2 is the predominant form of type IV collagenases while MMP-9 accounts for a minor amount [Puistola U, Ronnberg L, Martikainen H, Turpeenniemi-Hujanen T. (1989) *Hum Reprod*; Turpeenniemi-Hujanen T, Ronnberg L, Kauppila A, Puistola U. (1992) *Fertil Steril*; Turpeenniemi-Hujanen T, Feinberg R F, Kauppila A, Puistola U. (1995) *Fertil Steril*]; after the blastocysts implant into the endometrium and before placentation is complete in the first trimester, human trophoblasts produce both MMP-2 and MMP-9 [Polette M, Nawrocki B, Pintiaux A, Massenat C, Maquoi E, Volders L, Schaaps J P, Birembaut P, Foidart J M. (1994) *Lab Invest*; Shimonovitz S, Hurwitz A, Dushnik M, Anteby E, Geva-Eldar T, Yagel S. (1994) *Am J Obstet Gynecol*; Librach C L, Feigenbaum S L, Bass K E, Cui T, Verastas N, Sadovsky Y, Quigley J P, French D L, Fisher S J. (1994) *J Biol Chem*; Cross J C, Werb Z, Fisher S J. (1994) *Science*; Fisher S J, Cui T Y, Zhang L, Hartman L, Grahl K, Zhang G, Tarpey J, Damsky C H. (1989) *J Cell Biol*; Xu P. et al. (2000) *Biol Reproduct*].

The peculiarity of the fetal extracellular matrix is that up to 22 weeks it does not contain elastin, and during this period in ECM dominated fibronectin, and contain of collagen type IV does not differ from the level in adults [Coolen N. A., Schouten K., Middelkoop E., Ulrich M. (2010) *Arch Dermatol Res*]. Therefore, it was important to examine not only the proteolytic but also fibrinolytic and collagenolytic activities of the extract of abortive placental tissue that in our studies, as well as proteolysis, were significantly higher in placenta than in the internal organs of the fetus. Fibronectin degraded by tissue type plasminogen activator and urokinase [Marchina E., Barlati S. (1996) *Int J Biochem Cell Biol*.]. Studies in non-human systems have proposed a critical role for trophoblast-secreted plasminogen activator (PA) during implantation and placentation. PA activity in vascular and extracellular spaces is modulated by PA inhibitors (PAIs). PA-PAI interactions modulate trophoblast invasion in vivo and control fibrinolysis within the intervillous spaces of the placenta. Studies to examine the synthesis and regulation of PAI-1 and PAI-2 in normal human cytotrophoblasts revealed that PAI-1 and PAI-2 mRNA and protein are produced by cultured cytotrophoblasts. PAI-2 was localized by immunocytochemistry to villous syncytiotrophoblasts whereas PAI-1 was present primarily in invasive trophoblasts of implantation sites. These findings suggest that u-PA and PAI-1 are specifically required for the trophoblast invasive process [Kliman H. J. Trophoblast Infiltration (1994)].

Thus, our findings are consistent with the literature and suggests that abortive placental extract has a high proteolytic, fibrinolytic and collagenolytic activity, it can be used for the purpose of degradation of the extracellular matrix of fetal organs to isolate progenitor cells.

Consequent step was to study the amount of cells from different organs of the fetus can be obtained by perfusion of the autologous placenta tissue extract. Utilizing the novel method of fetal progenitor cells separation using natural collagenolytic and proteolytic activity of abortive placenta, as described herein, an abundant number of viable cells from different organs is realized: from fetal liver ($40.0 \pm 5.36 \times 10^6$ per 1 g tissue), kidney ($34.3 \pm 4.80 \times 10^6$ per 1 g tissue), spleen ($32.9 \pm 5.03 \times 10^6$ per 1 g tissue) and lung ($15.6 \pm 2.98 \times 10^6$ per 1 g tissue). Additional yields include the following: from fetal ileum $36.8 \pm 3.75 \times 10^5$ cells per 1 g tissue, suprarenal glands—$40.8 \pm 5.19 \times 10^5$ cells per 1 g tissue, heart—$7.2 \pm 1.60 \times 10^5$ cells per 1 g tissue, thymus—$98.2 \pm 9.31 \times 10^5$ cells per 1 g tissue. Amount of separated cells increased after fetal placenta incubation in presence PGF2α, but viability of these cells dramatically decreased. (Accordingly, PGF2α-treated placenta extracts cells were not included in final study of fetal progenitor cells biosafety). Considering the weight of the organs 18-20 weeks fetus, total number of cells isolated according to the method consisted of: liver (weight from 10 till 15 g)—$40$-$60 \times 10^7$, kidney (weight from 1.5 till 3.0 g)—$50$-$100 \times 10^6$, spleen (weight from 0.2 till 0.4 g)—$7$-$13 \times 10^6$, lung (weight from 6 till 9 g)—$90$-$140 \times 10^6$, heart (weight from 1.5 till 2.5 g)—$1$-$2 \times 10^6$, thymus (weight from 0.3 till 0.6 g)—$3$-$6 \times 10^6$, which is sufficient for organ-specific cell therapy without prior multiplication of progenitor cell.

The use of progenitor cells for cell therapy requires, first of all, an evaluation of their safety. The single-dose data demonstrates the absence of fetal progenitor cells toxic effects after their intravenous introduction (rat) and intraperitoneal injection (mice). In additional, no toxic effect were observed in blood system of Wistar rats. Weak expressive activation of erythropoiesis was observed in bone marrow. In peripheral blood insignificantly increases level of hemoglobin without reliable changes in quantity of erythrocytes, and decreased erythrocytes sedimentation rate were observed. Following an increase in the dosage of fetal progenitor cells, moderate expressive activation of erythropoiesis was observed in bone marrow. Also, following an increase in the dosage of fetal progenitor cells, increased level of haemoglobin, along with a trend toward an increase in quantity of erythrocytes and reduction in erythrocytes sedimentation rate was observed in peripheral blood. Intravenous injection of human fetal progenitor cells did not show toxic effects on the blood system in immunosuppressed Grey Giant rabbits; and in bone marrow weak expressive activation of erythropoiesis was observed. In peripheral blood, insignificant increase in level of hemoglobin without reliable changes of erythrocytes quantity, and reduction of erythrocytes sedimentation rate were noted. Administration of busulfan in Grey Giant rabbits of caused to sharp depression of hemopoiesis in bone marrow that characterizes pancytopenia and accompanied in peripheral blood erythropenia (anemia), hemoglobinpenia, thrombocytopenia, leukopenia, and relative increase level of neutrophils, absolute lymphopenia and absolute monocytopenia. Intravenous introduction of human fetal progenitor cells in busulfan-immunosuppressed Grey Giant rabbits, during 120 days effectively restores bone-marrow hemopoiesis and removes all of the above disorders in peripheral blood. Transplantation of human fetal progenitor cells in intact rats did not result in toxic effects on spermatogenic epithelium of testes. On the contrary, after introduction of human fetal progenitor cells, a stimulation of spermatogenesis via parameters of spermatogenesis index and fructose content in the anterior part of the prostates was observed. Busulfan shows expressed toxic effect in the reproductive system of the Wistar line male rats: Under the influence of this immunosuppressor mass of testes decreases to 2.0 times, concentration of testosterone in blood plasma—to 4.1 times, content of biological active luteinizing hormone in blood— to 2.0 times, activity of 3$\beta$-hydroxyl-$\Delta^5$-steroid-dehydrogenase reduces to 27%, concentration of spermatozoids in epididymises—to 2.1 times, index of spermatogenesis—to 2.3 times, content of fructose in the anterior part of prostates—to 26%. Transplantation of fetal progenitor cells, performed subsequently to injecting busulfan to animals, correspondingly deteriorates toxic effect of this immunosuppressor in the reproductive system of male rats, but repeated transplantation of human fetal progenitor cells completely restores as such hormonal regulation of spermatogenesis, similarly and functional condition of spermatogenic epithelium of the testes.

Thus, isolated fetal progenitor cells by the proposed new method do not have toxic effect, no carcinogenic, no hematotoxic, no myelotoxic, and do not have negative effect on the organs of reproductive system.

REFERENCE

Baraghini G. F., Celani M. F., Zaidi A. K. et al. (1984) "Problems associated with the in vitro bioassay of serum luteinizing hormone (LH) on mouse Leydig cell preparations: methodological aspects" *J Endocrinol Invest* 7(3): 23-31.

Bjorn S. F., Hastrup N., Lund L. R., Dano K., Larsen J. F., Pyke C. (1997) "Co-ordinated expression of MMP-2 and its putative activator, MT1-MMP, in human placentation" *Mol Hum Reprod* 3: 713-23.

Bryant-Greenwood G. D., Yamamoto S. Y. (1995) "Control of peripartal collagenolysis in the human chorion-decidua" *Am J Obstet Gynecol* 172: 63-70.

Coolen N. A., Schouten K., Middelkoop E., Ulrich M. (2010) "Comparison between human fetal and adult skin" *Arch Dermatol Res* 302: 47-55.

Cross J. C., Werb Z., Fisher S. J. (1994) "Implantation and the placenta: key pieces of the development puzzle" *Science* 266: 1508-18.

Draper D., McGregor J., Hall J., Jones W., Beutz M., Heine R. P. et al. (1995) "Elevated protease activities in human amnion and chorion correlate with preterm premature rupture of membranes" *Am J Obstet Gynecol* 173:1506-12.

Fisher S. J., Cui T. Y., Zhang L., Hartman L., Grahl K., Zhang G., Tarpey J., Damsky C. H. (1989) "Adhesive and degradative properties of human placental cytotrophoblast cells in vitro" *J Cell Biol* 109: 891-902.

Hiden U., Glitzner E., Ivanisevic M., Djelmis J., Wadsack Ch., Lang U., Desoye G. (2008) "MT1-MMP expression in first-trimester placental tissue is upregulated in type 1 diabetes as a result of elevated insulin and tumor necrosis factor-$\alpha$ levels" *Diabetes* 57: 150-7.

Hulboy D. L., Rudolph L. A., Matrisian L. M. (1997) "Matrix metalloproteinases as mediators of reproductive function" *Mol Hum Reprod* 3: 27-45.

Kliman H. J. "Trophoblast Infiltration" (1994) New Haven, Conn.—38 p.

Kochetov G. A. (1980) "Practical guidance by enzymology"—Moscow: High School.—266 p.

Librach C. L., Feigenbaum S. L., Bass K. E., Cui T., Verastas N., Sadovsky Y., Quigley J. P., French D. L., Fisher S. J. (1994) "Interleukin-1beta regulates human cytotrophoblast metalloproteinase activity and invasion in vitro" *J Biol Chem* 269: 17125-31.

Lowry J. H., Rosebrough N. J., Farr A. L., Randall R. J. (1951) "Protein measurement with the Folin phenol reagent" *J Biol Chem* 193: 265-75.

Marchina E., Barlati S. (1996) "Degradation of human plasma and extracellular matrix fibronectin by tissue type plasminogen activator and urokinase" *Int J Biochem Cell Biol* 28(10): 1141-50.

Maymon E., Romero R., Pacora P., Gervasi M. T., Gomez R., Edwin S. S., Yoon B. H. (2000) "Evidence of in vivo differential bioavailability of the active forms of matrix metalloproteinases 9 and 2 in parturition, spontaneous rupture of membranes, and intra-amniotic infection" *Am J Obstet Gynecol* 183:887-94.

Polette M., Nawrocki B., Pintiaux A., Massenat C., Maquoi E., Volders L., Schaaps J. P., Birembaut P., Foidart J. M. (1994) "Expression of gelatinases A and B and their tissue inhibitors by cells of early and term human placenta and gestational endometrium" *Lab Invest* 71: 838-46.

Puistola U., Ronnberg L., Martikainen H., Turpeenniemi-Hujanen T. (1989) "The human embryo produces basement membrane collagen (type IV collagen)-degrading protease activity" *Hum Reprod* 4: 309-11.

Purveyance of tissues of dead aborted fetuses is performed by Medical Termination of Pregnancy Rules, 2003 (G.S.R. 485(E)—In exercise of powers conferred by section 6 of the Medical Termination of Pregnancy Act, 1971 (34 of 1971), India.

Rajabi M. R., Dean D. D., Beydoun S. N., Woessner Jr. J. F. (1988) "Elevated tissue levels of collagenase during dilation of uterine cervix in human parturition" *Am J Obstet Gynecol* 159: 971-6.

Reznikov A. G., Demchenko V. M., Neshimenko O. V. (1976) "Influence of antitesticular cyto-toxic serum in formation of testosterone in testes of rats in normal and in hypogonadism, stipulating introduction of cadmium chloride" *Physiol J AS USSR* 5: 616-21.

Sanotckiy I. V., Fomenko V. N., Salnikova M. C. et al. (1978) "Methods of experimental investigation by establishment of thresholds action of industrial toxins in generative function with the aim of hygienic norms" *Method Recom* Moscow: Ministry of Health USSR.—25 p.

Shimonovitz S., Hurwitz A., Dushnik M., Anteby E., Geva-Eldar T., Yagel S. (1994) "Developmental regulation of the expression of 72 and 92 kDa type IV collagenases in human trophoblasts: a possible mechanism for control of trophoblast invasion" *Am J Obstet Gynecol* 171: 832-8.

Tsatas. D., Baker M. S., Rice G. E. (1999) "Differential expression of proteases in human gestational tissues before, during and after spontaneous onset labour at term" *J Reprod Fertil* 116:43-9.

Turpeenniemi-Hujanen T., Feinberg R. F., Kauppila A., Puistola U. (1995) "Extracellular matrix interactions in early human embryos: implications for normal implantation events" *Fertil Steril* 64: 132-8.

Turpeenniemi-Hujanen T., Ronnberg L., Kauppila A., Puistola U. (1992) "Laminin in the human embryo implantation: analogy to the invasion by malignant cells" *Fertil Steril* 58: 105-13.

Ukhov Yu. I., Astrakhancev A. F. (1983) "Morphological methods in the evaluation of condition of the testes" *Ach Anat Histol Embryol* LXXXIV, 3: 66-72.

Vadillo-Ortega F., Gonzalez-Avila G., Furth E. E., Lei H., Muschel R. J., Stetler-Stevenson W. G. et al. (1995) "92-kd type IV collagenase (matrix metalloproteinase-9) activity in human amniochorion increases with labor" *Am J Pathol* 146:148-56.

Van Damme M. P., Robertson D. M., Diczfalusy E. (1974) "An improved in vitro bioassay method for measuring luteinizing hormone (LH) activity using mouse Leydig cell preparations" *Acta Endocrinol* 77: 655-71.

Volkova O. V., Eletckiy Yu. K. (1982) "Fundamentals of histology with histological techniques".—Moscow: Medicine—304 p.

Vul T. H, Werb Z. (2000) "Matrix metalloproteinases: effectors of development and normal physiology" *Gen Develop* 14: 2123-33.

Xu P., Alfaidy N., Challis J. R. (2002) "Expression of matrix metalloproteinase (MMP)-2 and MMP-9 in human placenta and fetal membranes in relation to preterm and term labor" *J Clin Endocrinol Metab* 87: 1353-61.

Xu P., Wang Y., Zhu S., Luo S., Piao Y., Zhuang L. (2000) "Expression of matrix metalloproteinase-2, -9, and -14, tissue inhibitors of metalloproteinase-1, and matrix proteins in human placenta during the first trimester" *Biol Reprod* 62: 988-94.

Yu W. H., Woessner Jr. J F. (2000) "Heparan sulfate proteoglycans as extracellular docking molecules for matrilysin (matrix metalloproteinase 7)" *J Biol Chem* 275: 4183-91.

What is claimed is:

1. A method of isolating progenitor cells from different organs of an aborted fetus by using natural collagenolytic, fibrinolytic and proteolytic activity of an autologous abortive placenta, the method comprising:

preparing a collagenolytic, fibrinolytic, and proteolytic fetal placenta extract by selecting chorionic villi tissue from the abortive placenta, incubating the tissue with PGF2α for activation of proteolytic activity, homogenizing the tissue, incubating with trypsin for activation of collagenase activity followed by addition of trypsin inhibitor; and isolating fetal progenitor cells from target organs of the aborted fetus by:
  performing an in situ three open-loop perfusion process of a fetus blood vascular system of the aborted fetus, wherein the perfusion process comprises removing blood from the fetus vascular system;
  lysing remaining blood cells in the fetus blood vascular system by perfusion with $NH_4Cl$, $KHCO_3$, and EDTA;
  perfusing the target organs with solution containing the collagenolytic, fibrinolytic, and proteolytic fetal placenta extract; and
  removing target organs and isolating cells by rupturing the organs, filtering, and pelleting cells to generate isolated fetal progenitor cells.

2. The method of claim 1, wherein the aborted fetus is aborted at 18-20 weeks of gestation.

3. The method of claim 1, wherein creating the solution comprises activating a proteolysis in placenta tissue by a trypsin short-term reaction which is stopped by a soybean trypsin inhibitor.

4. The method of claim 1, wherein a first loop of perfusion in the in situ three open-loop perfusion process comprises providing a maternal-fetal blood supply via an umbilical vein.

5. The method of claim 1, wherein a second loop of perfusion in the in situ three open-loop perfusion process comprises providing a blood supply route through a left ventricle of a heart.

6. The method of claim 1, wherein a third loop of perfusion in the in situ three open-loop perfusion process comprises providing a blood supply route through an abdominal part of an aorta.

7. The method of claim 1, wherein the three-open loop perfusion process begins in a femoral vein.

8. The method of claim 1, wherein the target organs comprise any of a liver, intestines, lungs, a kidney, suprarenal glands, a heart, a thymus, and a spleen.

* * * * *